A compound, a method of imaging a cell, and a method of detecting a cancer, an inflammatory disease, or a neoplastic disease are provided. The compound includes a nitroxide derivative of a fluorophore that is activatable upon exposure to free radicals. The method of imaging a cell includes contacting the cell with an activatable nitroxide derivative of a fluorophore. The method of detecting a cancer, an inflammatory disease, or a neoplastic disease includes administering an activatable nitroxide derivative of a fluorophore and then imaging one or more cells contacted with the compound.

(12) United States Patent
Uddin et al.

(10) Patent No.: US 10,792,377 B2
(45) Date of Patent: Oct. 6, 2020

(54) COMPOUNDS AND METHOD FOR IMAGING CANCER

(71) Applicant: Vanderbilt University, Nashville, TN (US)

(72) Inventors: Jashim Uddin, Nashville, TN (US); Brenda C. Crews, Franklin, TN (US); Lawrence J. Marnett, Nashville, TN (US)

(73) Assignee: Vanderbilt University, Nashville, TN (US)

( * ) Notice: Subject to any disclaimer, the term of this patent is extended or adjusted under 35 U.S.C. 154(b) by 0 days.

(21) Appl. No.: 15/944,735

(22) Filed: Apr. 3, 2018

(65) Prior Publication Data
US 2018/0280543 A1 Oct. 4, 2018

Related U.S. Application Data

(60) Provisional application No. 62/480,867, filed on Apr. 3, 2017.

(51) Int. Cl.
*A61K 49/00* (2006.01)
*A61K 51/00* (2006.01)
*C07D 491/22* (2006.01)

(52) U.S. Cl.
CPC ...... *A61K 49/0041* (2013.01); *A61K 49/0052* (2013.01); *C07D 491/22* (2013.01)

(58) Field of Classification Search
CPC ....... A61K 49/00; A61K 51/00; C07D 491/22
See application file for complete search history.

(56) References Cited

U.S. PATENT DOCUMENTS 7,736,624 B2 * 6/2010 Marnett ............... A61K 31/405
424/9.6

OTHER PUBLICATIONS

Eric L. Dane et al. Synthesis of a BDPA-TEMPO Biradical, Org. Lett, 1871-1874. (Year: 2009).*
Hyeran Lee, Walter Akers, Kumar Bhushan, Sharon Bloch, Gail Sudlow, Rui Tang, and Samuel Achilefu. Near-Infrared pH-Activatable Fluorescent Probes for Imaging Primary and Metastatic Breast Tumors. Bioconjugate Chem. 2011;22(4):777-784.
Yasuteru Urano, Daisuke Asanuma, Yukihiro Hama, Yoshinori Koyama, Tristan Barrett, Mako Kamiya, Tetsuo Nagano, Toshiaki Watanabe, Akira Hasegawa, Peter L Choyke, and Hisataka Kobayashi. Selective molecular imaging of viable cancer cells with pH-activatable fluorescence probes. Nature Med. 2009;15:104-109.
Giri K. Vegesna, Jagadeesh Janjanam, Jianheng Bi, Fen-Tair Luo, Jingtuo Zhang, Connor Olds, Ashutosh Tiwari and Haiying Liu. pH-Activatable near-infrared fluorescent probes for detection of lysosomal pH inside living cells. J. Mater. Chem. B. 2014;2:4500-4508.
Gun-Joong Kim, Doo-Ha Yoon, Mi-Yeon Yun, Hyockman Kwon, Hyun-Joon Haa, Hae-Jo Kim, An activatable fluorescent probe for targeting cellular membrane through the biothiol-mediated hydrazone-to-pyrazole transformation. Sensors Actuators B: Chem. 2015;211:245-249.
Zhang H. Fan J, Wang J, Zhang S, Dou B, Peng X. An off-on COX-2-specific fluorescent probe: targeting the Golgi apparatus of cancer cells. J. Am. Chem. Soc. 2013;135(31):11663-11669.
Uddin, M.J., Crews, B.C., Blobaum, A.L., Kingsley, P.J., Gorden, D.L., McIntyre, J.O., Matrisian, L.M., Subbaramaiah, K., Dannenberg, A.J., Piston, D.W., and Marnett, L.J. Selective Visualization of Cyclooxygenase-2 in Inflammation and Cancer by Targeted Fluorescent Imaging Agents. Cancer Res. 2010;70(9):3618-3627.
Uddin M.J., Crews B.C., Xu S., Ghebreselasie K., Daniel C.K., Kingsley P.J., Banerjee S., Marnett L.J.. Antitumor Activity of Cytotoxic Cyclooxygenase-2 Inhibitors. ACS Chem Biol. 2016;11(11):3052-60.
Neil J.R., Johnson K.M., Nemenoff R.A., Schiemann W.P.. Cox-2 inactivates Smad signaling and enhances EMT stimulated by TGF-beta through a PGE2-dependent mechanisms. Carcinogenesis. 2008;29(11):2227-35.

* cited by examiner

Primary Examiner — Michael G. Hartley
Assistant Examiner — Jagadishwar R Samala
(74) Attorney, Agent, or Firm — Stites & Harbison PLLC; Sean P. Ritchie

(57) ABSTRACT

20 Claims, 32 Drawing Sheets

Loaded Micellar
Nanoparticles (FQ-CA-NPs)

COMPOUNDS AND METHOD FOR IMAGING CANCER

RELATED APPLICATIONS

This application claims the benefit of U.S. Provisional Application Ser. No. 62/480,867, filed Apr. 3, 2017, the entire disclosure of which is incorporated herein by this reference.

GOVERNMENT INTEREST

This invention was made with government support under grant numbers CA89450 and CA136465 awarded by the National Institutes of Health. The government has certain rights in the invention.

TECHNICAL FIELD

The presently-disclosed subject matter relates to compounds useful for imaging cancer. In particular, the presently-disclosed subject matter relates to compounds useful as activatable COX-2 probes for imaging cancer.

BACKGROUND

Known imaging methods, such as angiography, computed tomography, magnetic resonance imaging, and radionuclide imaging, rely on contrast agents that are "always on." A unique aspect of optical imaging is that fluorescent probes can be designed to be activatable, so that they are only "turned on" under certain conditions. Probes that are activatable and also accumulate in the tumor in a targeted fashion could be ideal for detection of superficial tumors or tumors that can be accessed by endoscopy.

Fluorocoxib A (FA) is a COX-2 targeted optical imaging probe, which displays a high degree of selectivity of uptake in the COX-2-positive tumors over COX-2-negative tumors. Fluorocoxib A or B (FA or FB) are "always on" type fluorophores allowing target specific detection of inflammation and solid tumors. Unfortunately, targeted signals from these compounds are always hampered by strong noise from non-targeted normal tissues/organs due to distribution and inefficient clearance of probes (FA or FB).

Accordingly, there remains a need for selective, activatable fluorescent probes.

SUMMARY

The presently-disclosed subject matter meets some or all of the above-identified needs, as will become evident to those of ordinary skill in the art after a study of information provided in this document.

This summary describes several embodiments of the presently-disclosed subject matter, and in many cases lists variations and permutations of these embodiments. This summary is merely exemplary of the numerous and varied embodiments. Mention of one or more representative features of a given embodiment is likewise exemplary. Such an embodiment can typically exist with or without the feature(s) mentioned; likewise, those features can be applied to other embodiments of the presently-disclosed subject matter, whether listed in this summary or not. To avoid excessive repetition, this summary does not list or suggest all possible combinations of such features.

Provided herein, in some embodiments is a compound comprising a structure according to formula I:

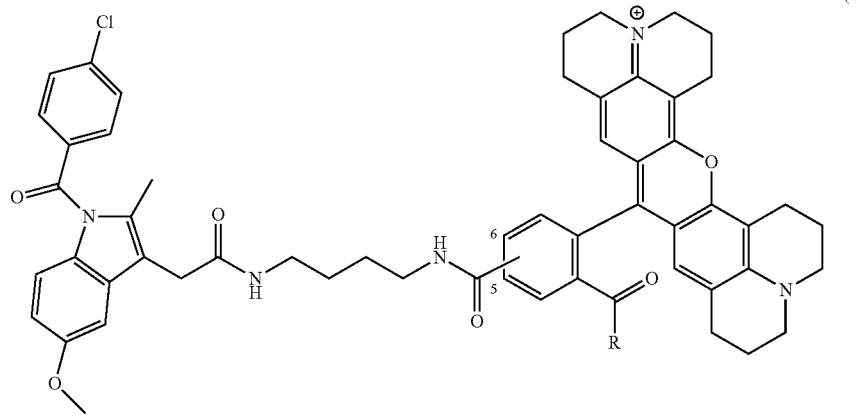

wherein R is selected from O⁻,

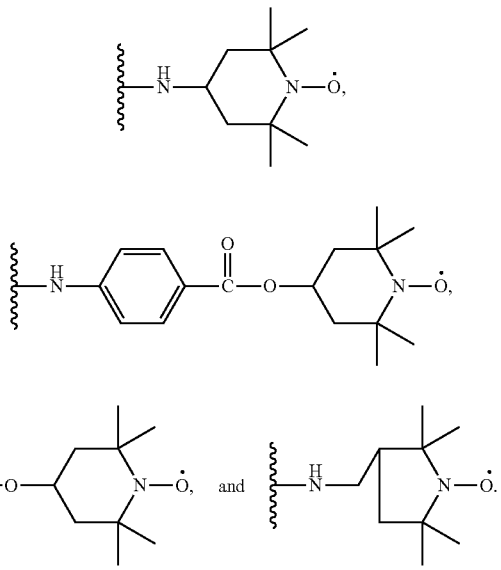

In one embodiment, the compound is a 5-isomer.

In one embodiment, the compound is a 6-isomer.

In some embodiments, R is selected from the group consisting of

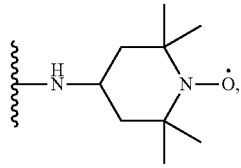

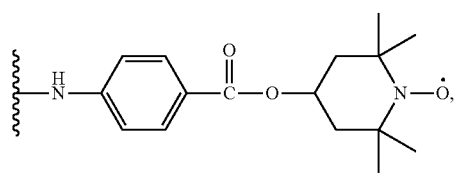

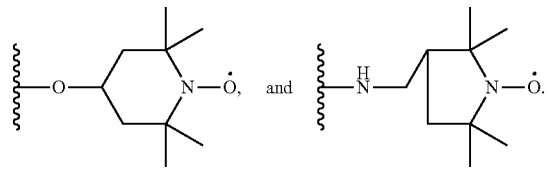

In one embodiment, R is

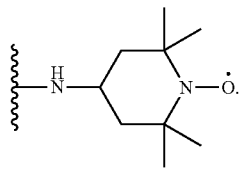

In another embodiment, the compound is a 5-isomer. In another embodiment, the compound is a 6-isomer. In one embodiment, R is

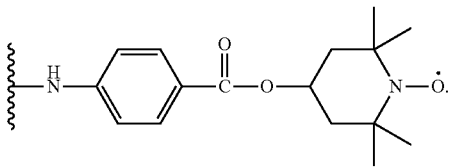

In another embodiment, the compound is a 5-isomer. In another embodiment, the compound is a 6-isomer. In one embodiment, R is

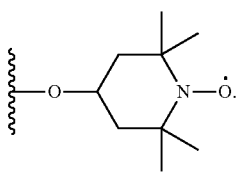

In one embodiment, R is In another embodiment, the compound is a 5-isomer. In another embodiment, the compound is a 6-isomer. In one embodiment, R is

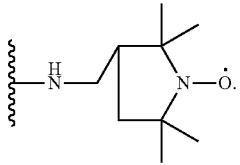

In another embodiment, the compound is a 5-isomer. In another embodiment, the compound is a 6-isomer.

Also provided herein, in some embodiments, is a method of imaging a cell, the method comprising contacting the cell with a compound comprising a structure according to formula I:

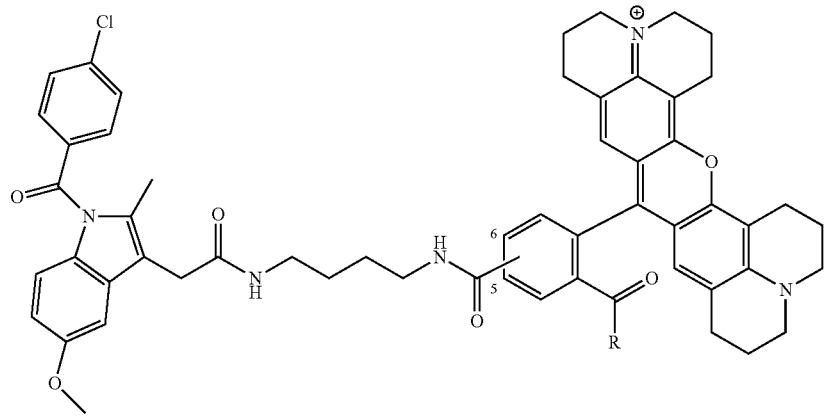

(I)

wherein R is selected from O⁻,

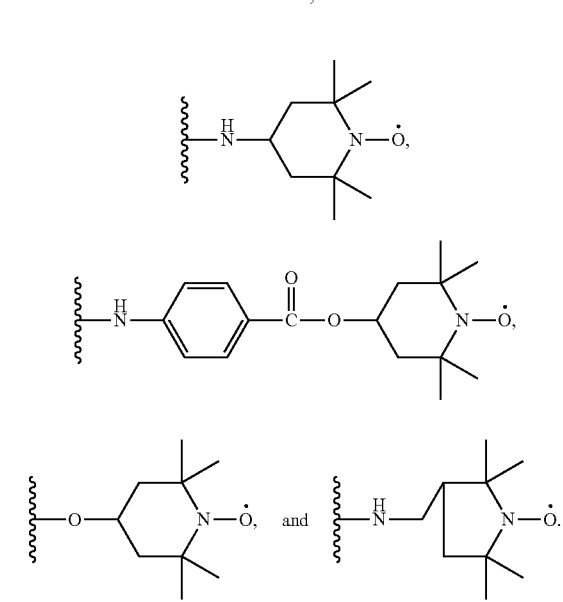

In one embodiment, the compound is a 5-isomer. In one embodiment, the compound is a 6-isomer. In one embodiment, the cell is a tumor cell. In another embodiment, the tumor cell is in vivo.

Further provided herein, in some embodiments, is a method of detecting a cancer, an inflammatory disease, or a neoplastic disease, the method comprising administering an activatable compound and then imaging one or more cells contacted with the compound. In one embodiment, the activatable compound comprises a structure according to formula I:

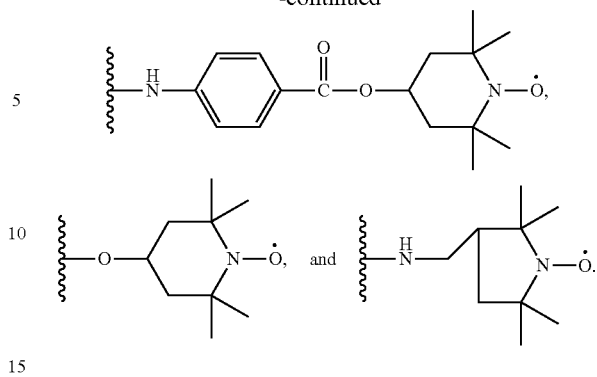

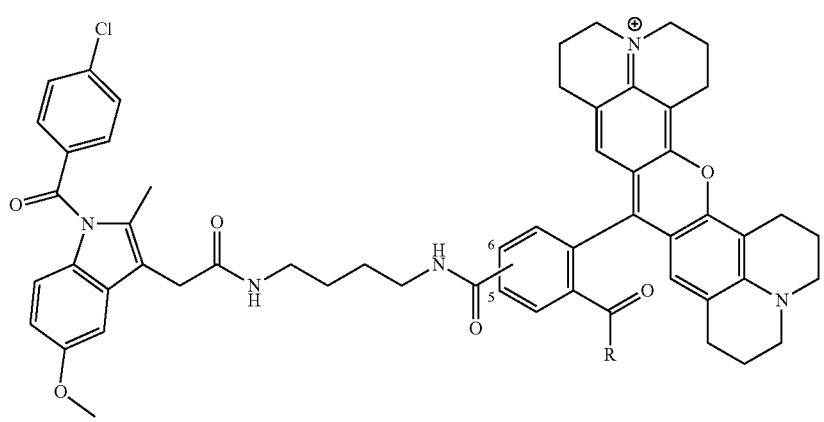

(I)

wherein R is selected from O⁻,

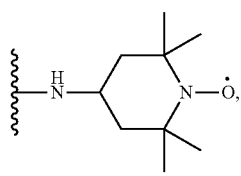

Figure 7:
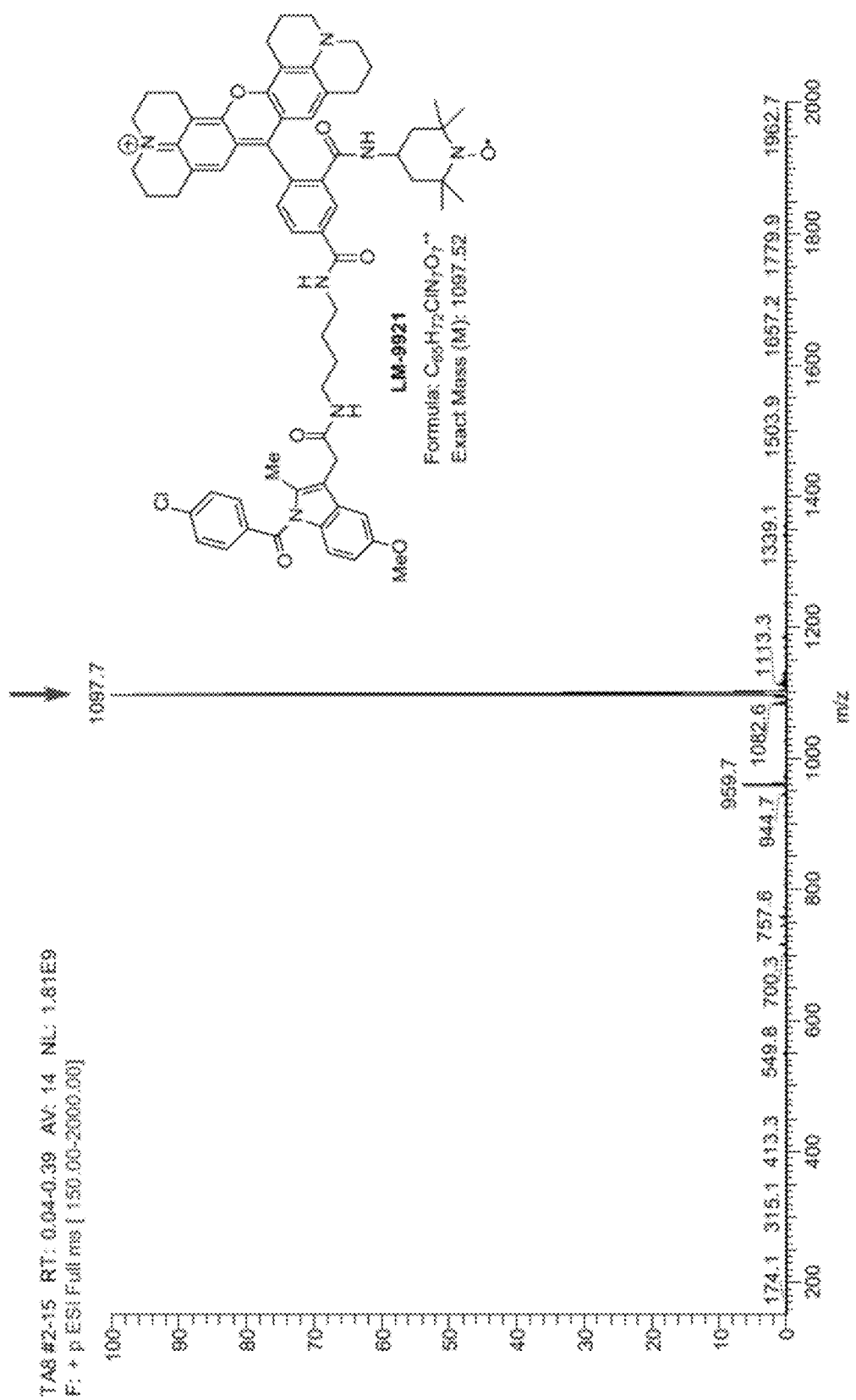

FIG. 7 shows an image illustrating mass spectrometry of fluorocoxib Q1.

Figure 8:
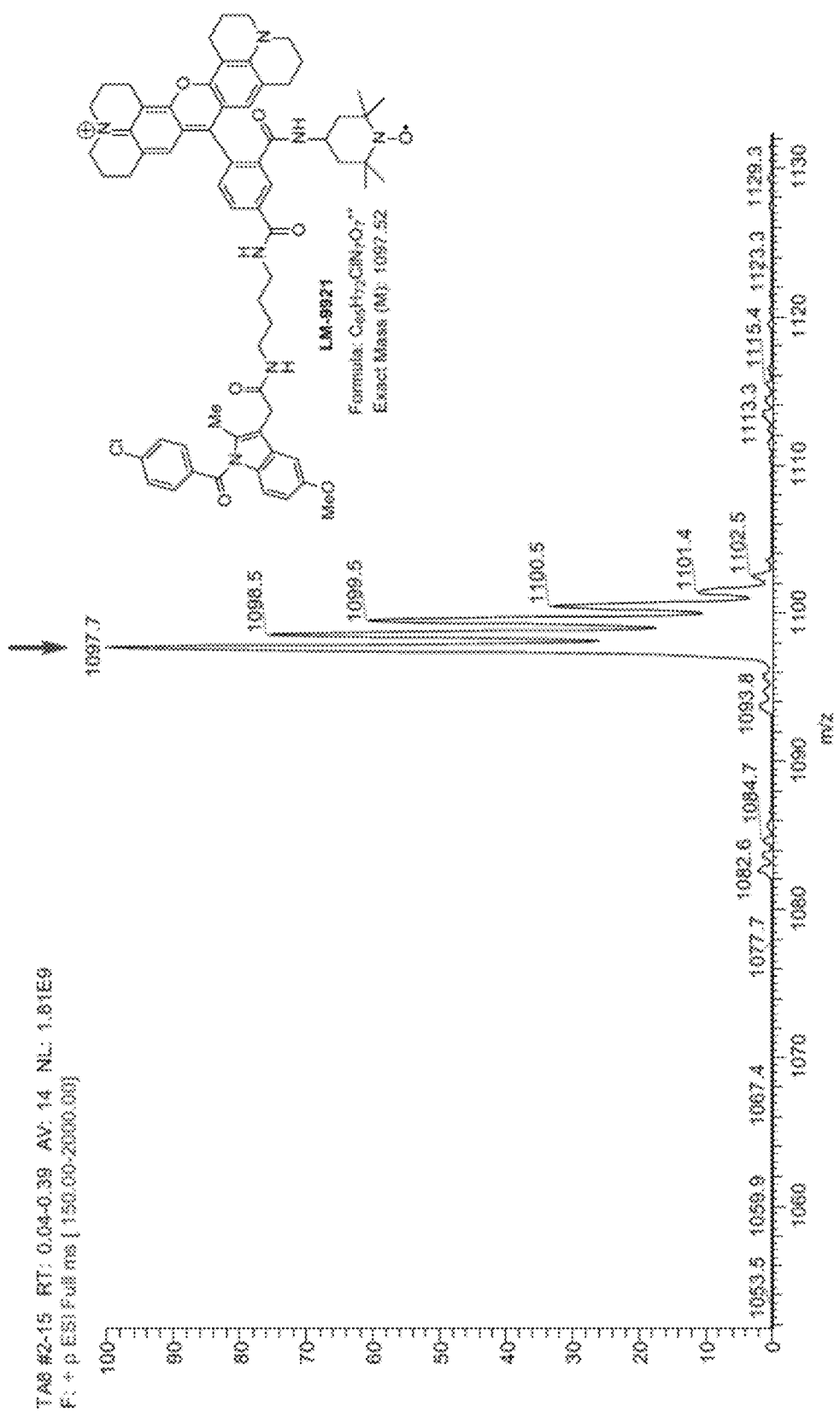

FIG. 8 shows an image illustrating an enhanced view of the mass spectrometry of FIG. 7.

Figure 9:
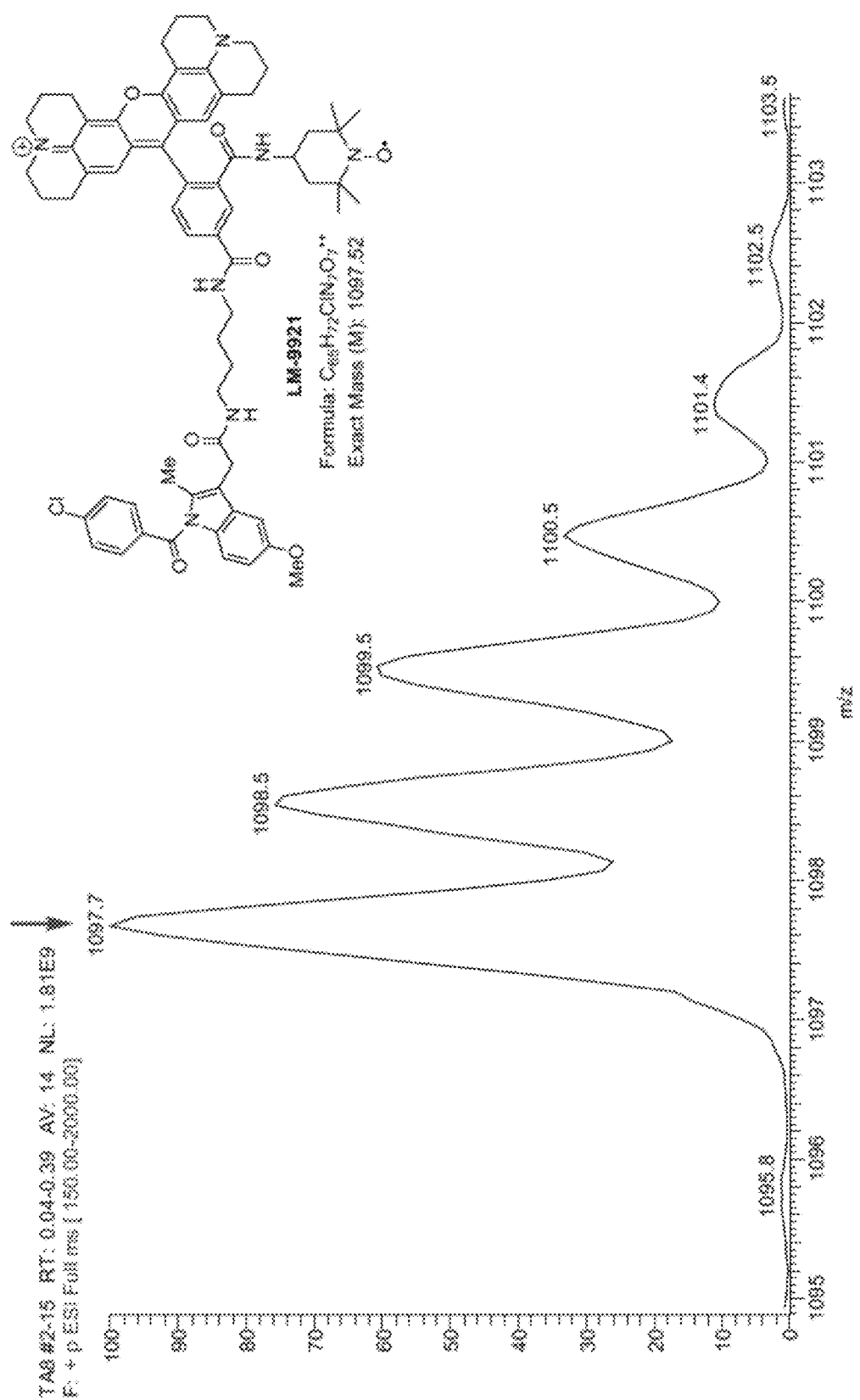

FIG. 9 shows an image illustrating an enhanced view of the mass spectrometry of FIG. 7.

Figure 10:
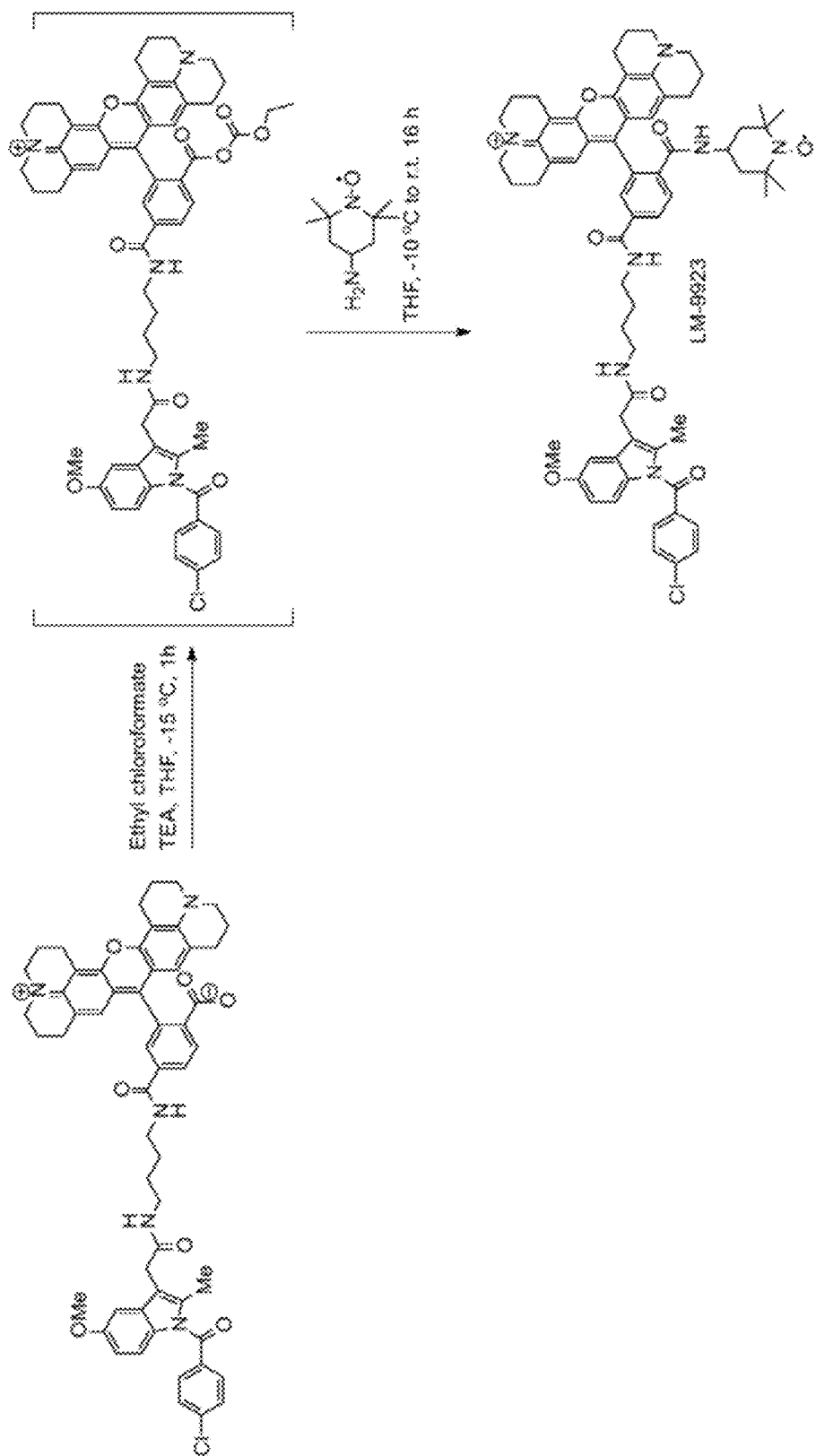

FIG. 10 shows a schematic view illustrating synthesis of fluorocoxib Q2, according to an embodiment of the disclosure.

Figure 11:
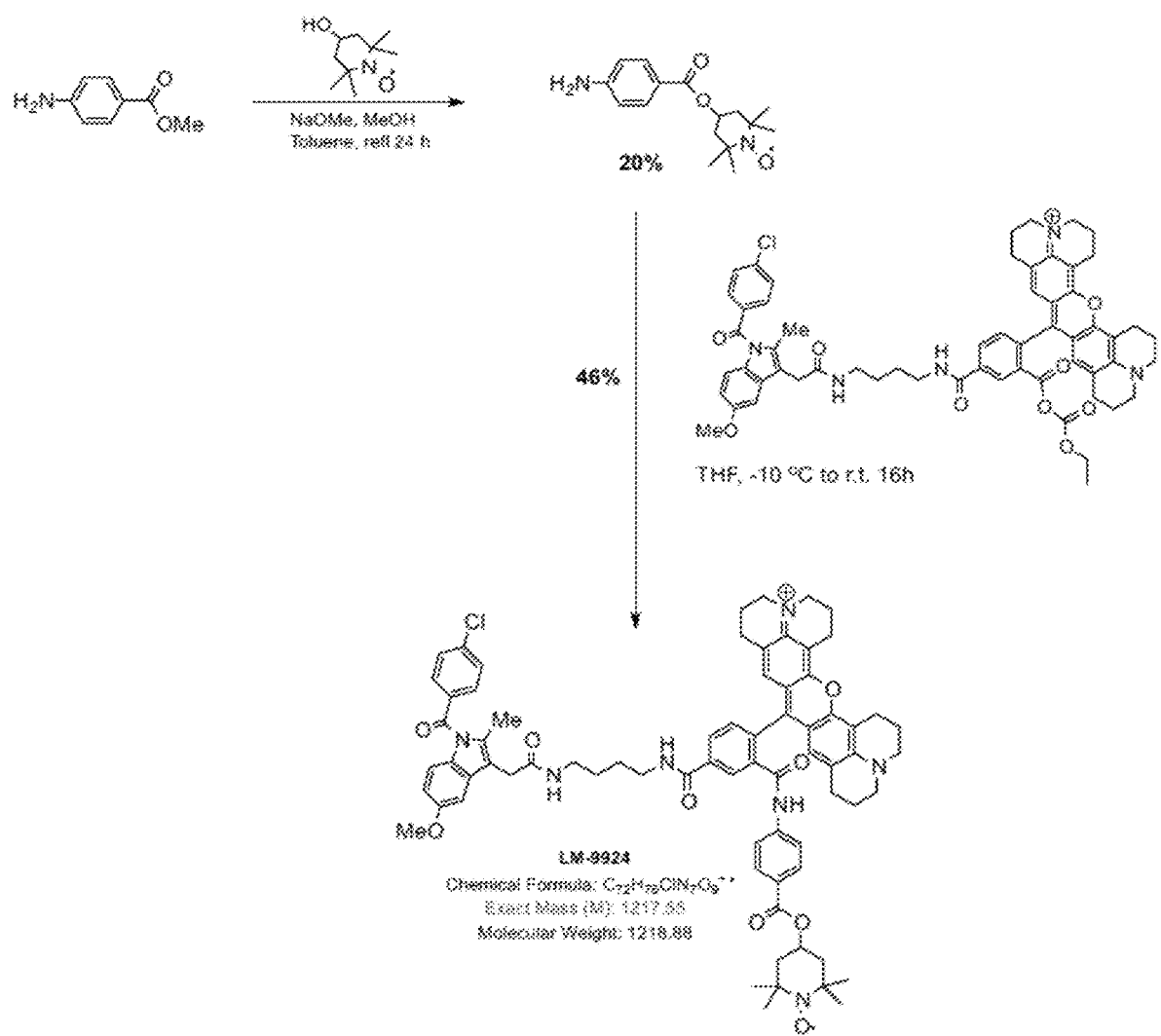

FIG. 11 shows a schematic view illustrating synthesis of fluorocoxib Q3, according to an embodiment of the disclosure.

Figure 12:
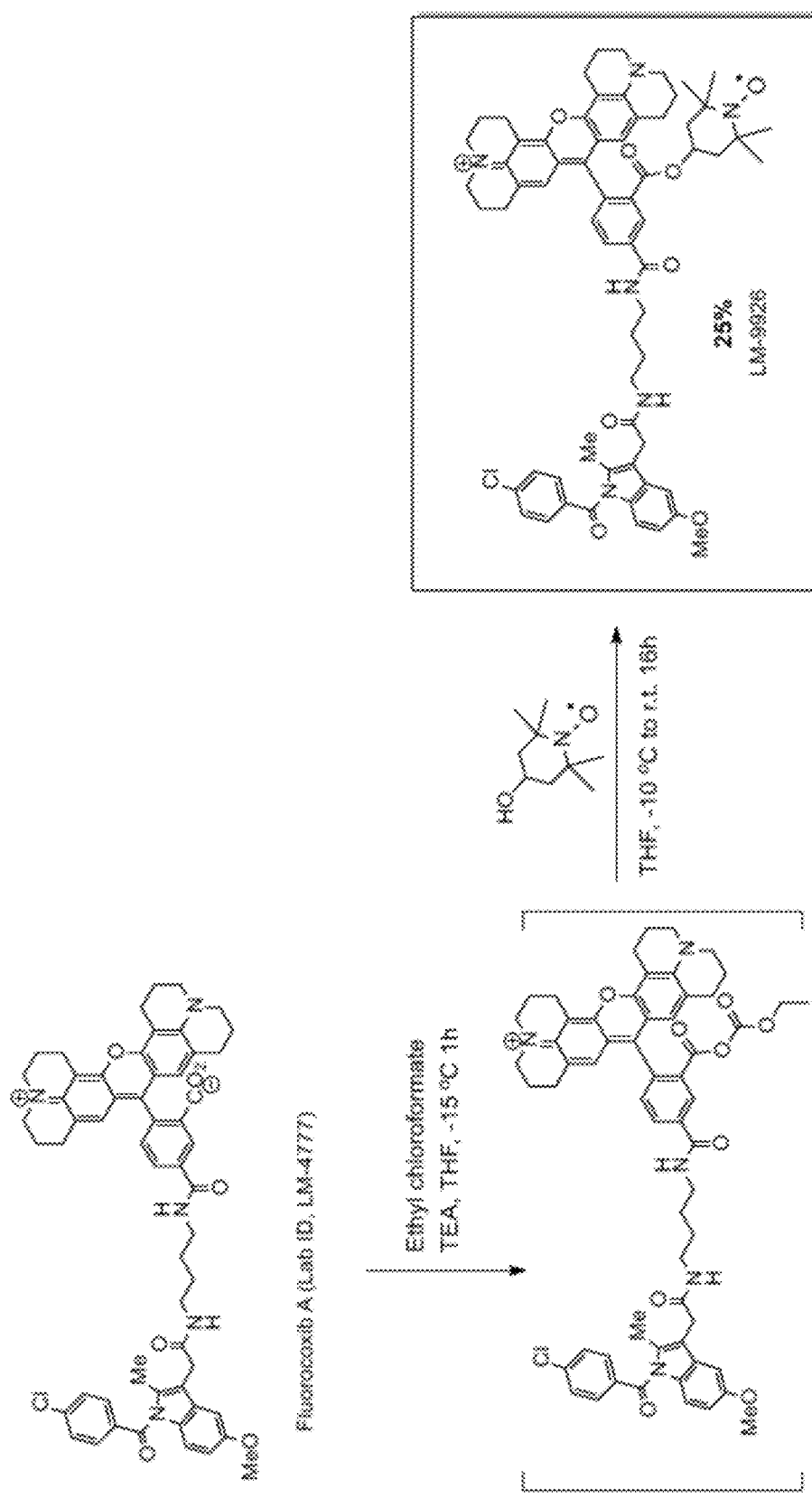

FIG. 12 shows a schematic view illustrating synthesis of fluorocoxib Q4, according to an embodiment of the disclosure.

Figure 13:
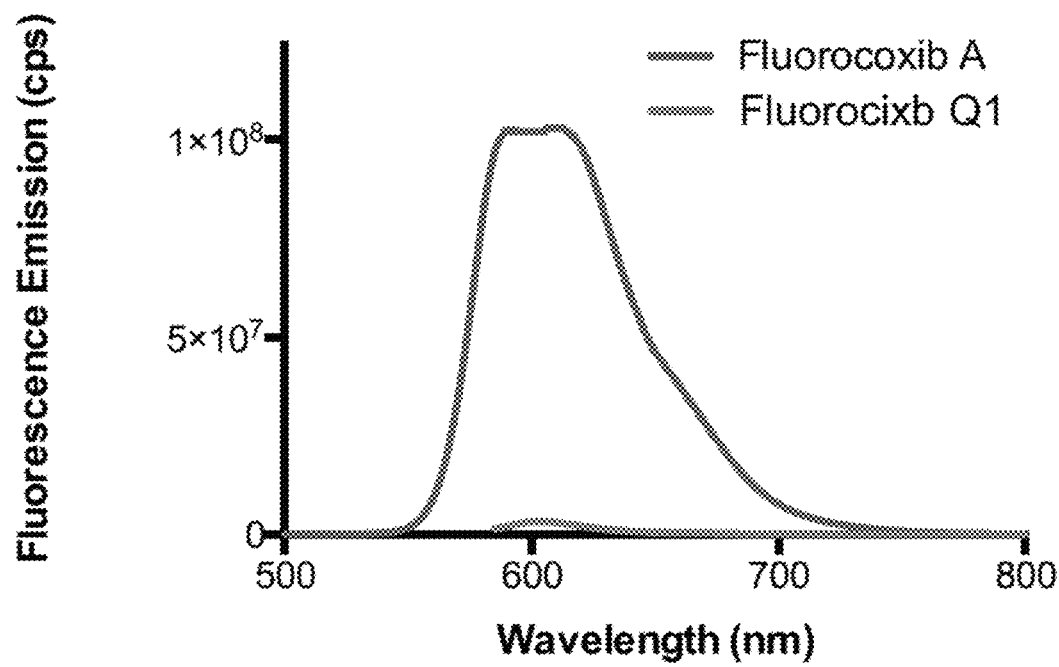

FIG. 13 shows a graph illustrating fluorescence emission of fluorocoxib A and fluorocoxib Q1.

Figure 14:
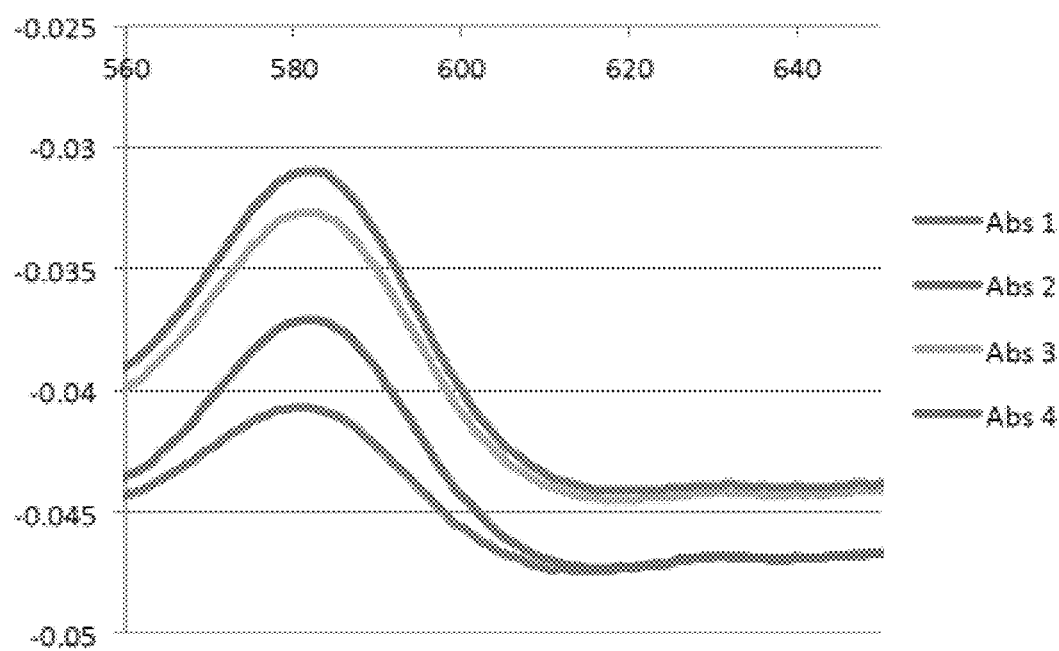

FIG. 14 shows a graph illustrating time-dependent absorbance of fluorocoxib Q1 treated with DMSO/EtOH, according to an embodiment of the disclosure.

Figure 15:
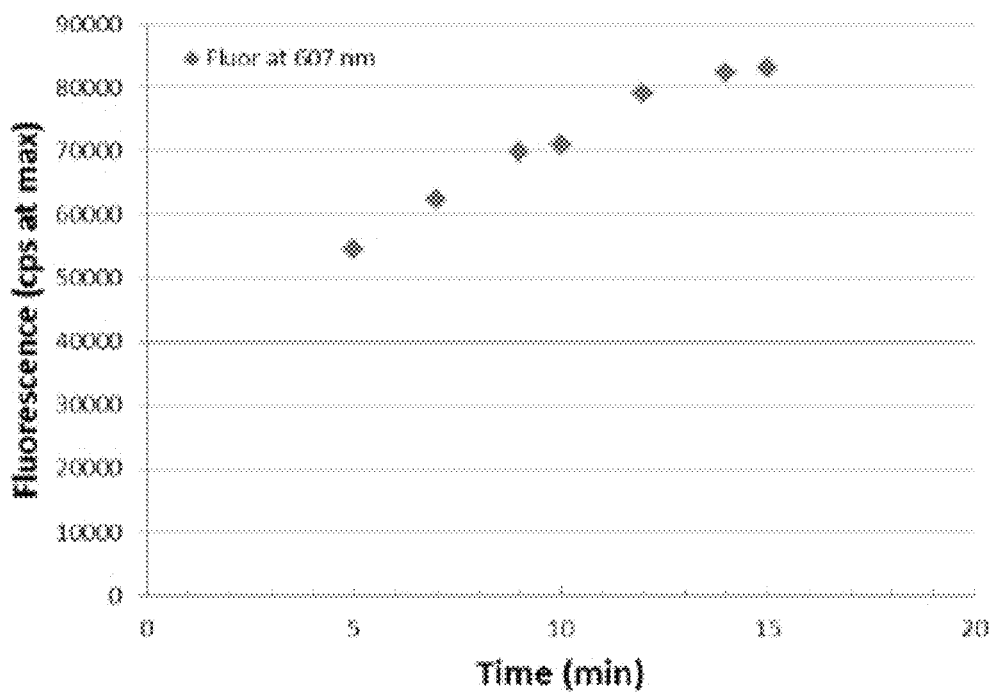

FIG. 15 shows a graph illustrating time-dependent fluorescence of fluorocoxib Q1 treated with DMSO/EtOH, according to an embodiment of the disclosure.

Figure 16:
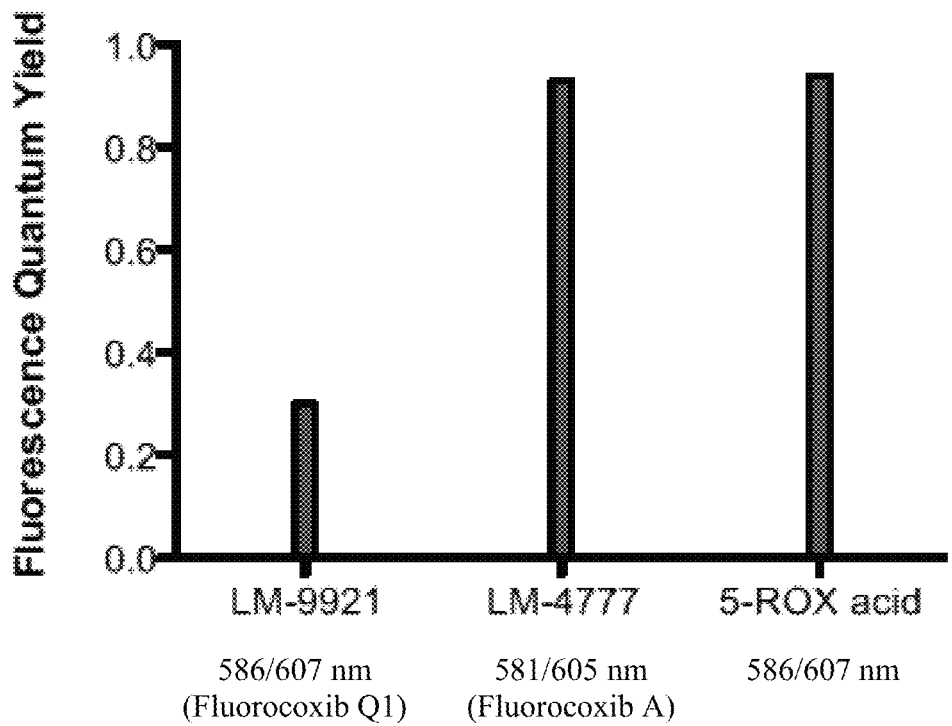

FIG. 16 shows a graph illustrating fluorescence quantum yield for various compounds treated with DMSO/EtOH according to an embodiment of the disclosure.

Figure 17:
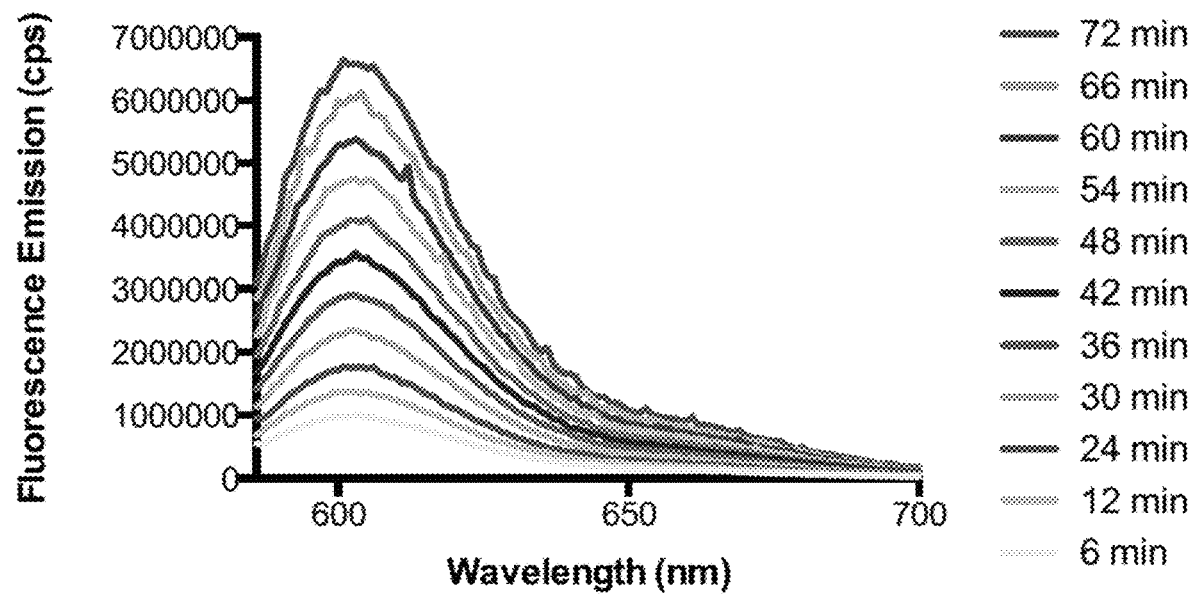

FIG. 17 shows a graph illustrating time-dependent fluorescence of fluorocoxib Q1 treated with ascorbic acid, according to an embodiment of the disclosure.

Figure 18:
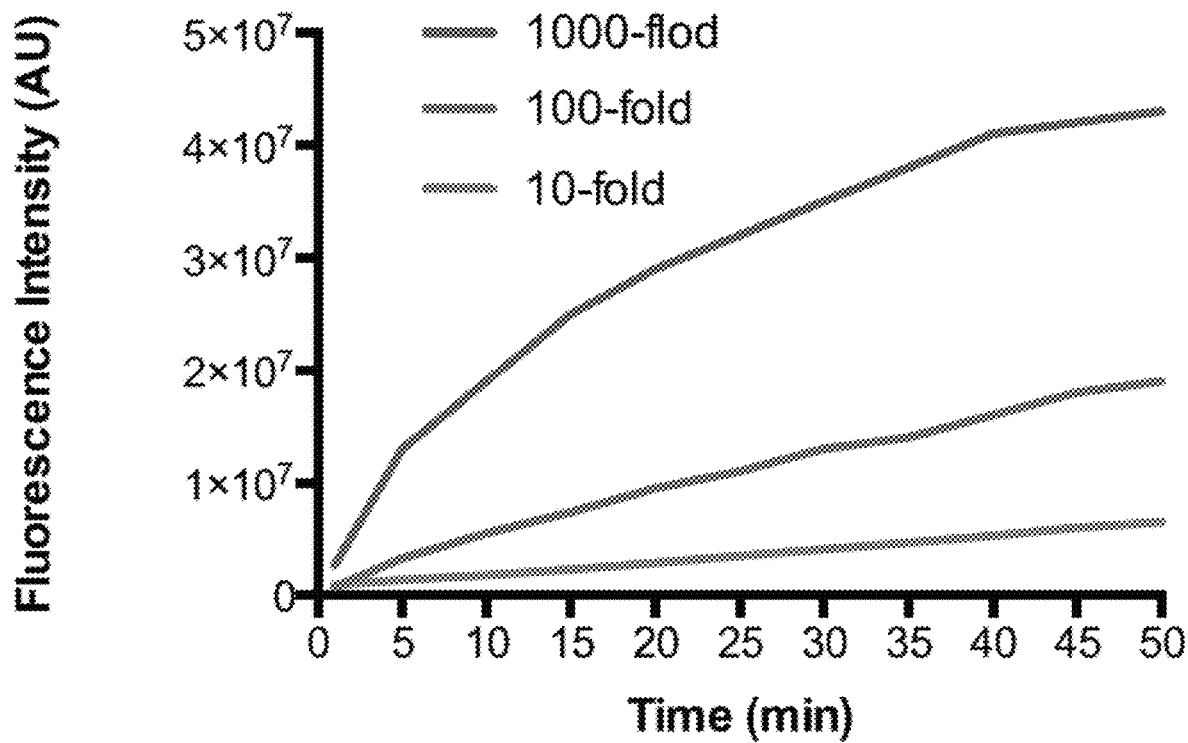

FIG. 18 shows a graph illustrating ascorbic acid concentration-dependent fluorescence of fluorocoxib Q1, according to an embodiment of the disclosure.

Figure 19:
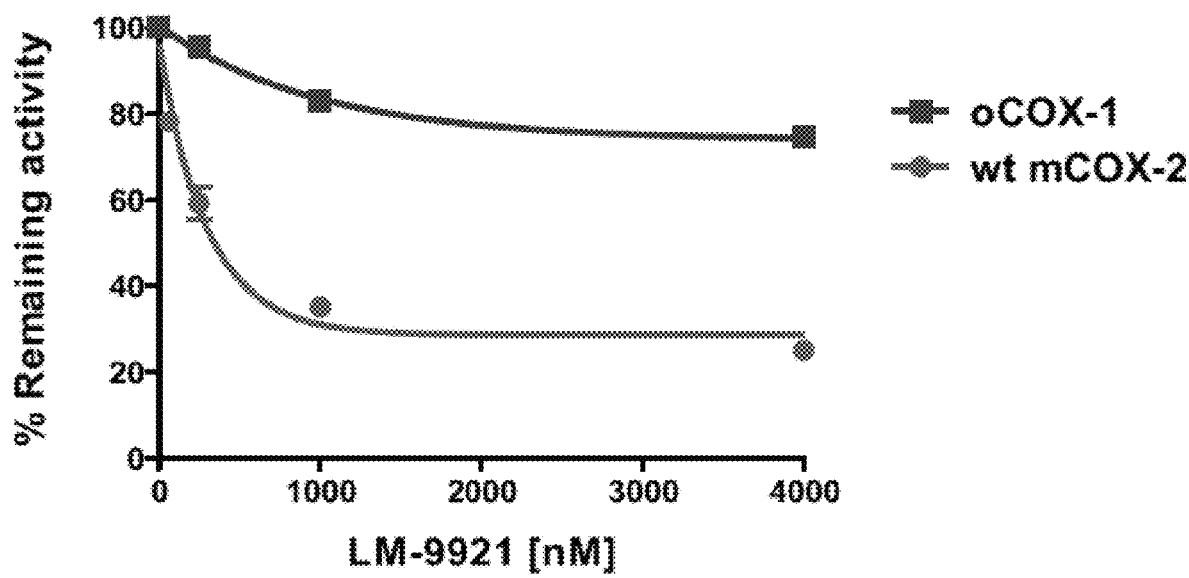

FIG. 19 shows a graph illustrating inhibition of COX-1 or COX-2 by fluorocoxib Q1 in an in vitro purified cox assay. Exact mass of fluorocoxib Q1-1097.53; Molecular weight of fluorocoxib Q1-1098.76; COX-2 $IC_{50}$-303 nM.

Figure 20:
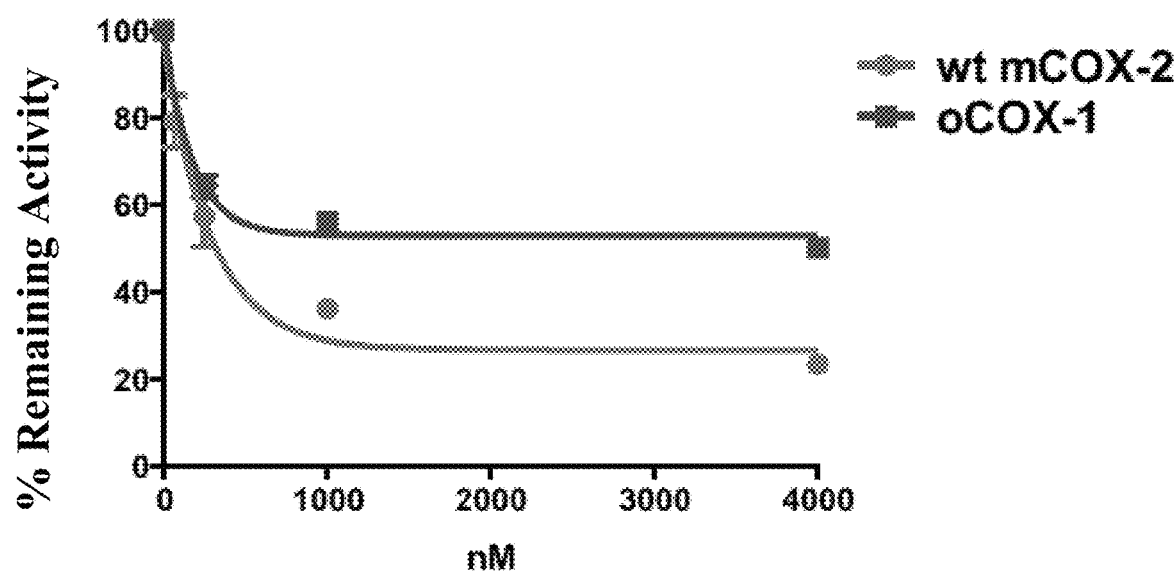

FIG. 20 shows a graph illustrating inhibition of COX-1 or COX-2 by fluorocoxib Q2 in an in vitro purified cox assay. Exact mass of fluorocoxib Q2-1097.53; Molecular weight of fluorocoxib Q2-1098.77; COX-2 $IC_{50}$-332 nM.

Figure 21:
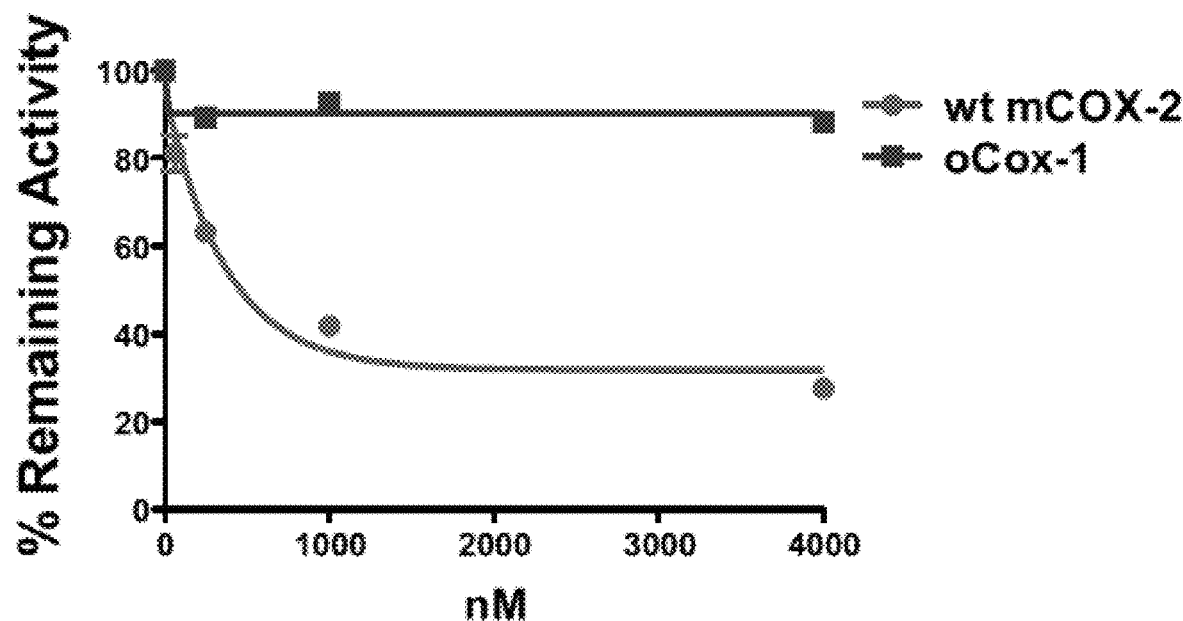

FIG. 21 shows a graph illustrating inhibition of COX-1 or COX-2 by fluorocoxib Q3 in an in vitro purified cox assay. Exact mass of fluorocoxib Q3-1217.55; Molecular weight of fluorocoxib Q3-1218.88; COX-2 $IC_{50}$-460 nM.

Figure 22:
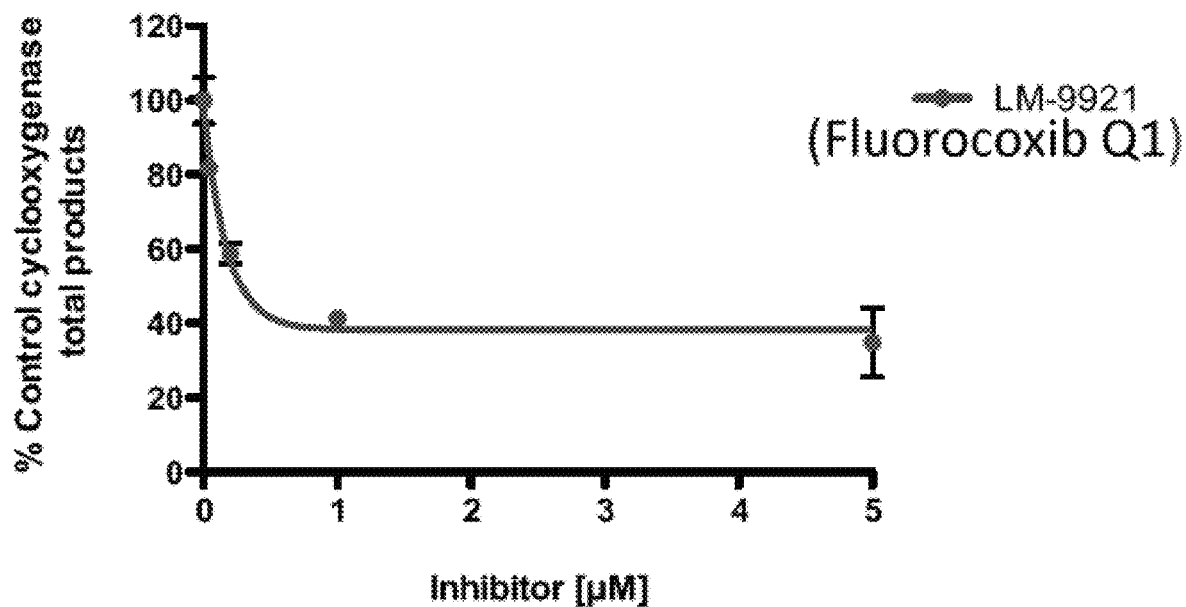

FIG. 22 shows a graph illustrating in vitro fluorocoxib Q1 inhibition of hCOX-2 in 1483 cells (8 μM $^{14}$C-AA, 30 min at 37° C.). hCOX-2 $IC_{50}$-285 nM.

Figure 23:
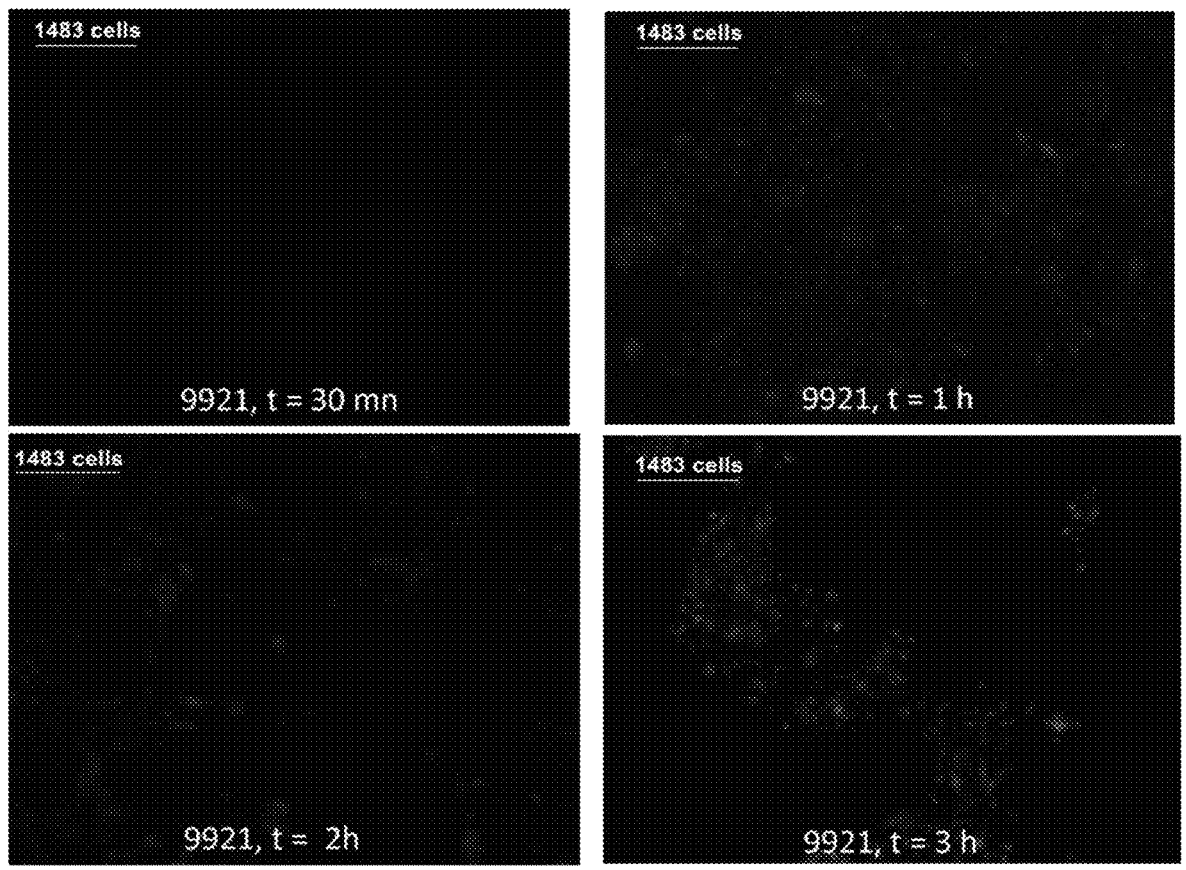

FIG. 23 shows fluorescence microscopy images illustrating fluorescence of fluorocoxib Q1 in 1483 cells at 0.5, 1, 2, and 3 hours.

Figure 24:
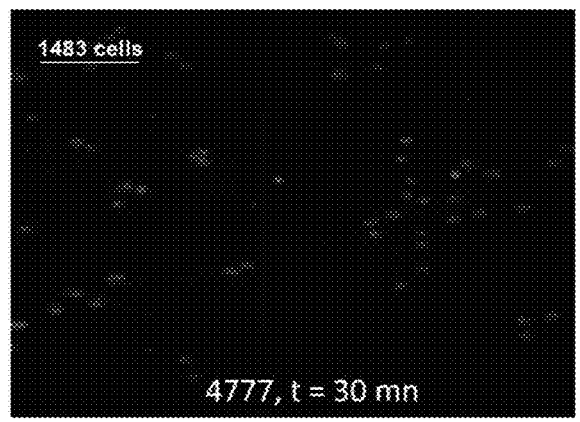

FIG. 24 shows a fluorescence microscopy image illustrating fluorescence of fluorocoxib A in 1483 cells at 0.5 hours.

Figure 25:
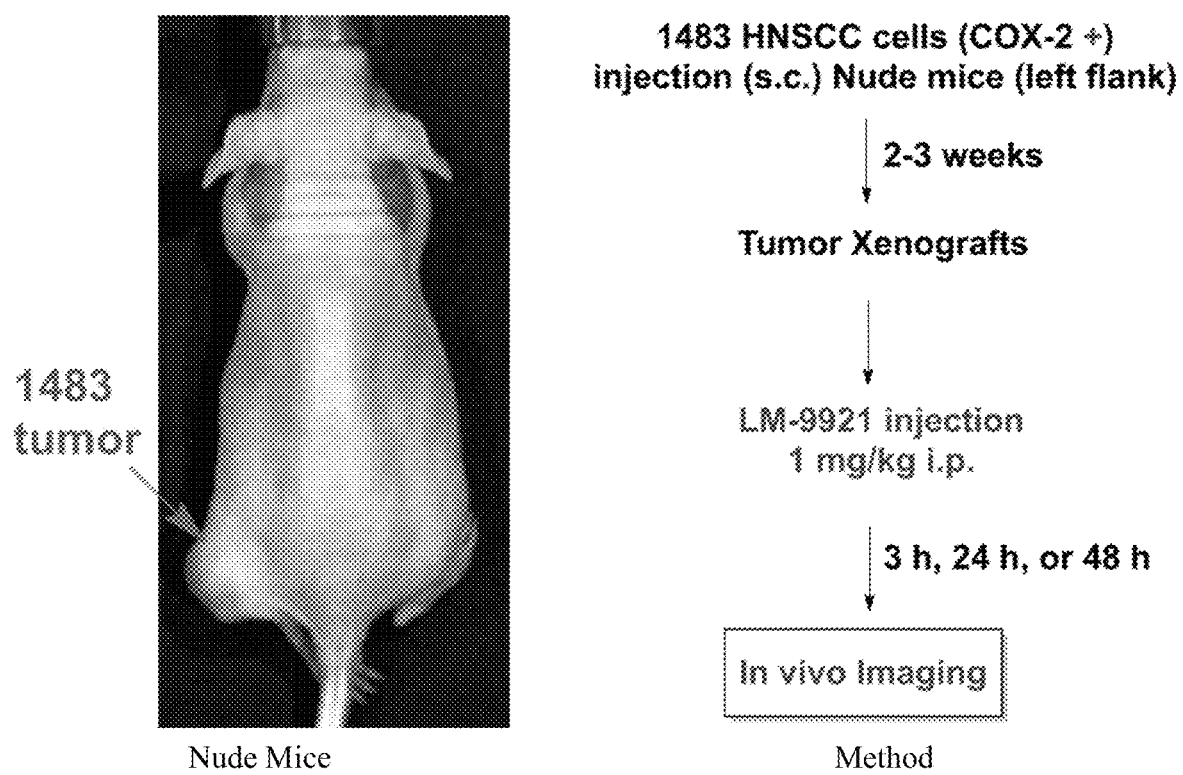

FIG. 25 shows an image and schematic view of a method of in vivo imaging, according to an embodiment of the disclosure.

Figure 26A:
Figure 26B:
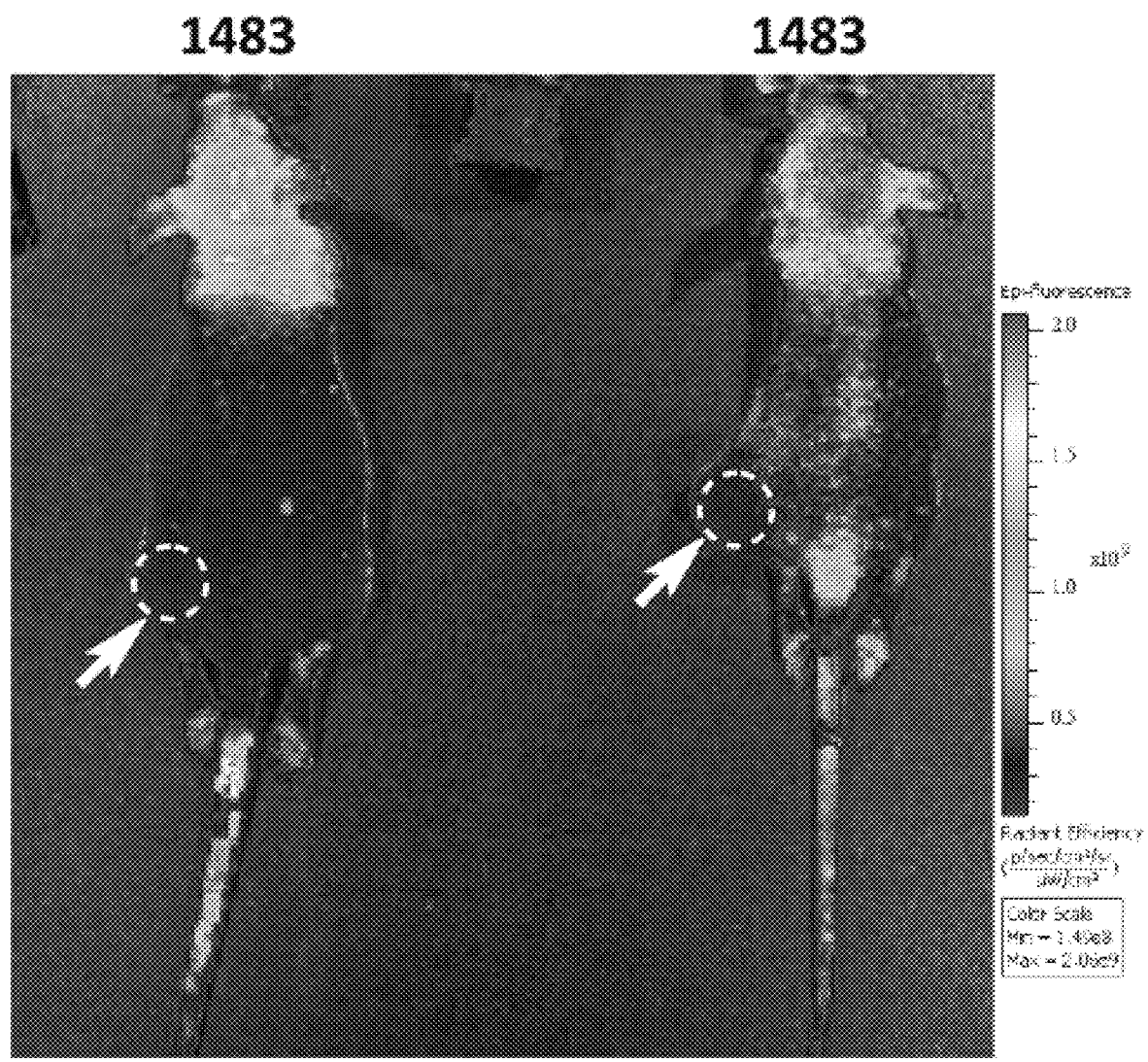

FIGS. 26A-B show images illustrating fluorescence of (A) fluorocoxib A and (B) fluorocoxib Q1 in nude mice 1483 xenografts at 3 hours post-injection. The images were taken with a DsRed filter, 1 s, f/2. Fluorocoxib A and fluorocoxib Q1 were dosed at 1 mg/kg, intraperitoneal.

Figure 27A:
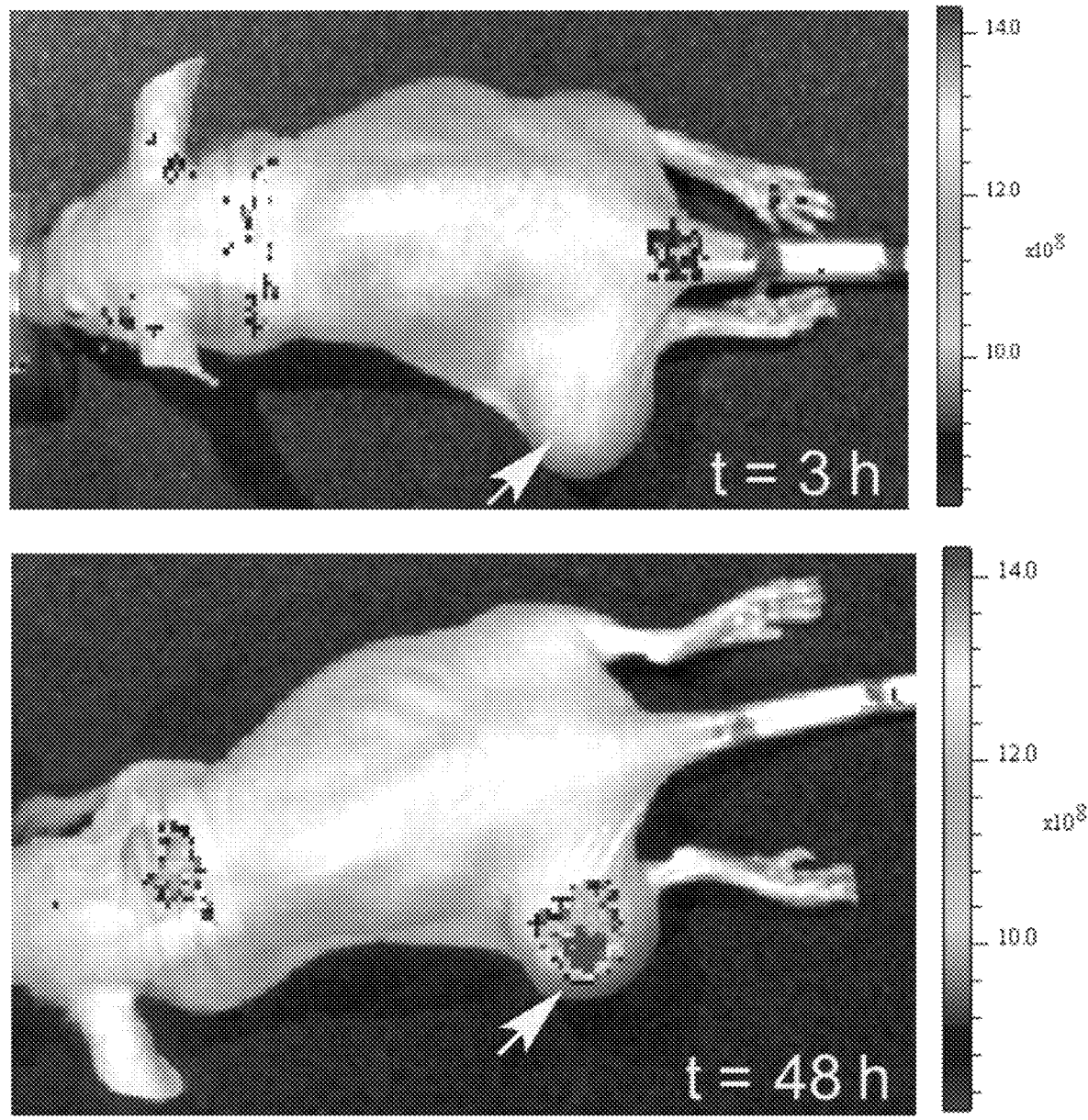
Figure 27B:
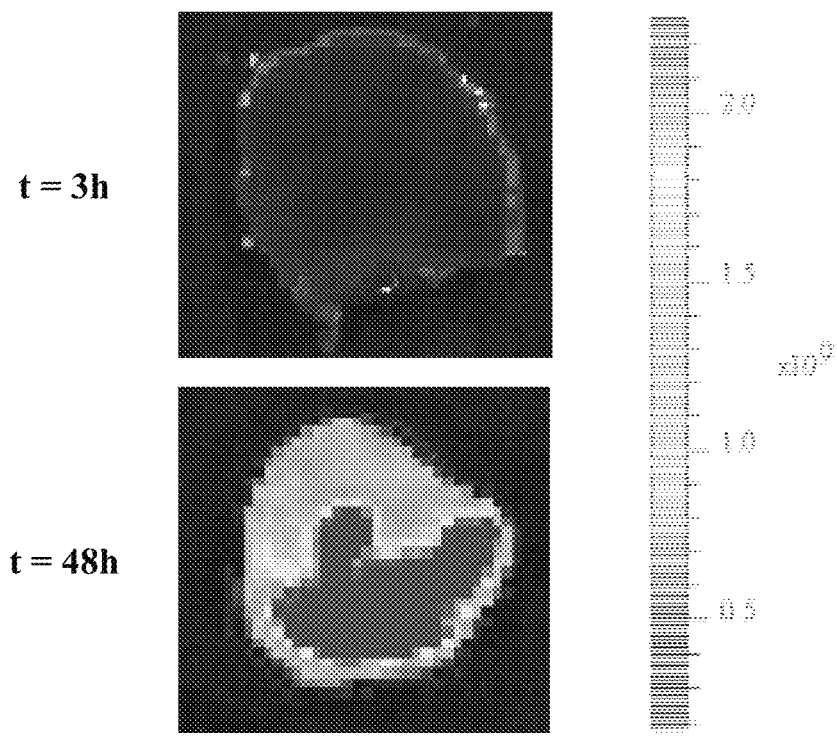
Figure 27C:
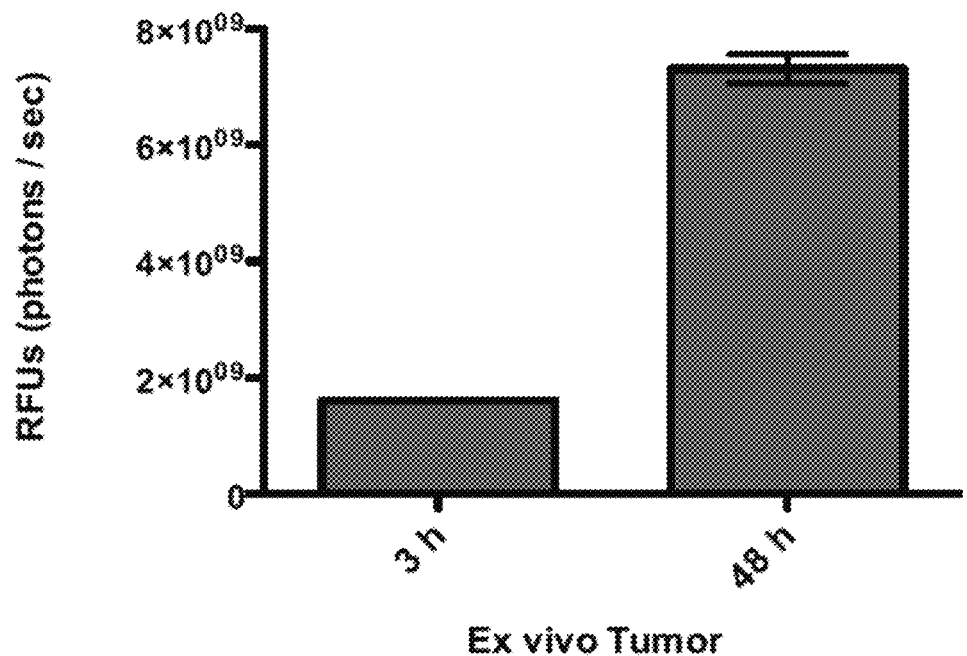

FIG. 27A-C show graphs and images illustrating imaging of COX-2 expressing xenografts by fluorocoxib Q1. (A) shows images illustrating in vivo time-course of fluorocoxib Q1. Nude mice bearing 1483 HNSCC xenografts were dosed with fluorocoxib Q1 (1 mg/kg, i.p.) and imaged in vivo at 3 hours and 48 hours post-injection. (B) shows images of 1483 HNSCC tumor xenografts surgically collected from nude mice at 3 hours and 48 hours post injection and imaged ex vivo. (C) shows a graph illustrating image analyses of 3 hour versus 48 hour xenografts (n=8, p=0.002).

Figure 28:
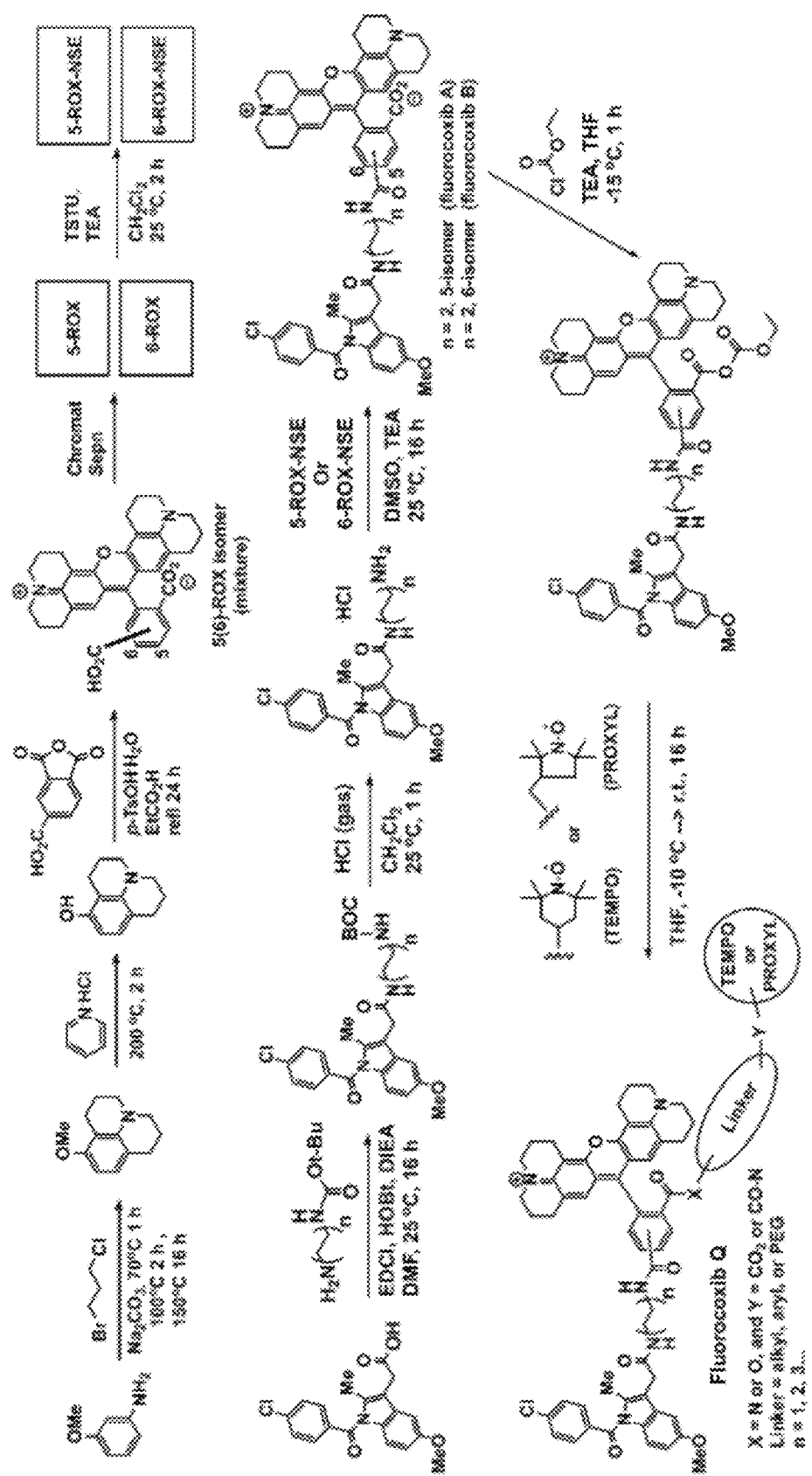
Figure 29A:
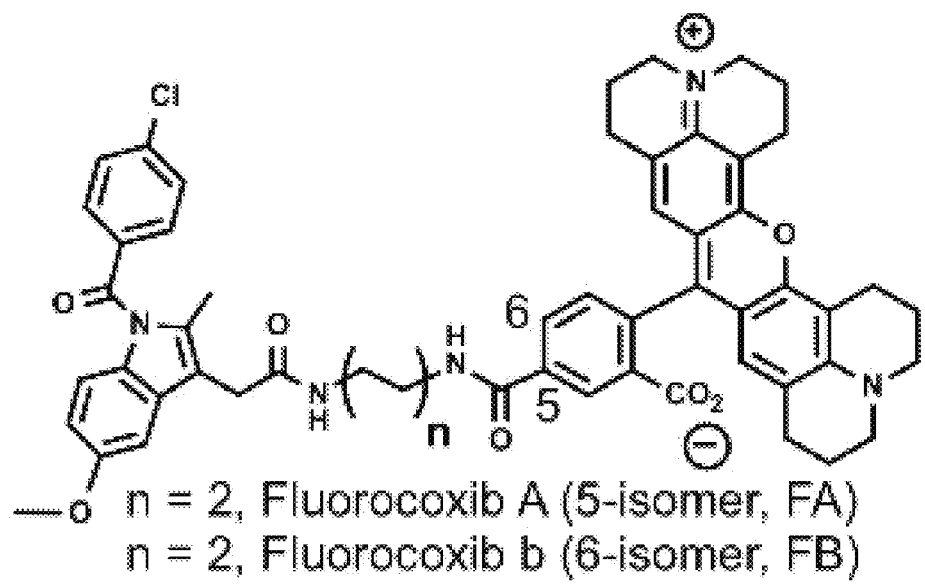
Figure 29B:
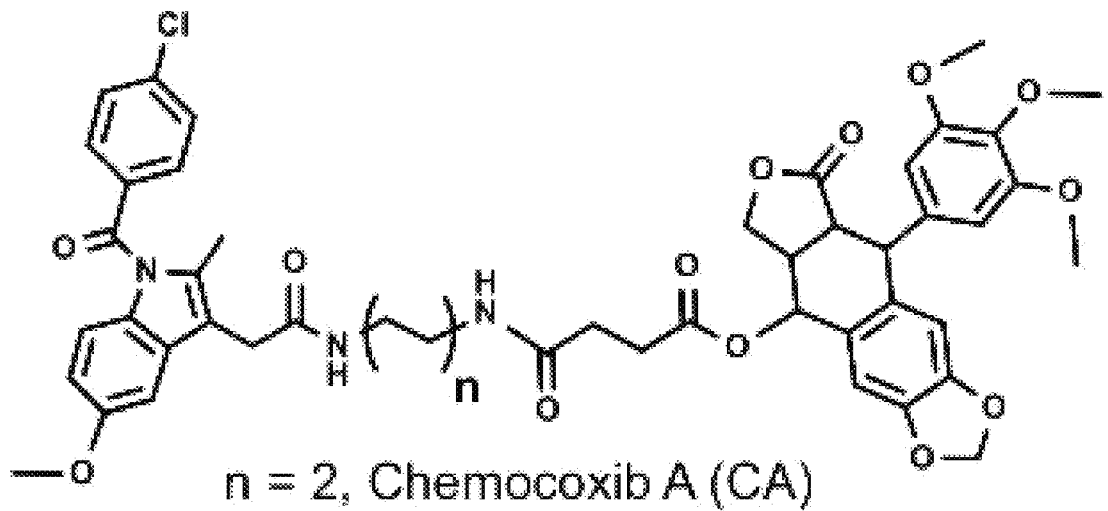
Figure 29C:
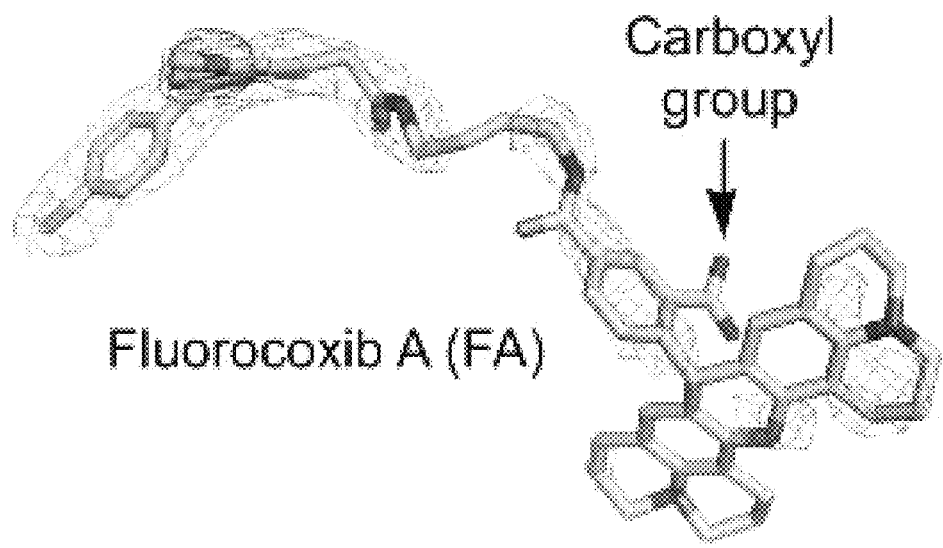
Figure 29D:
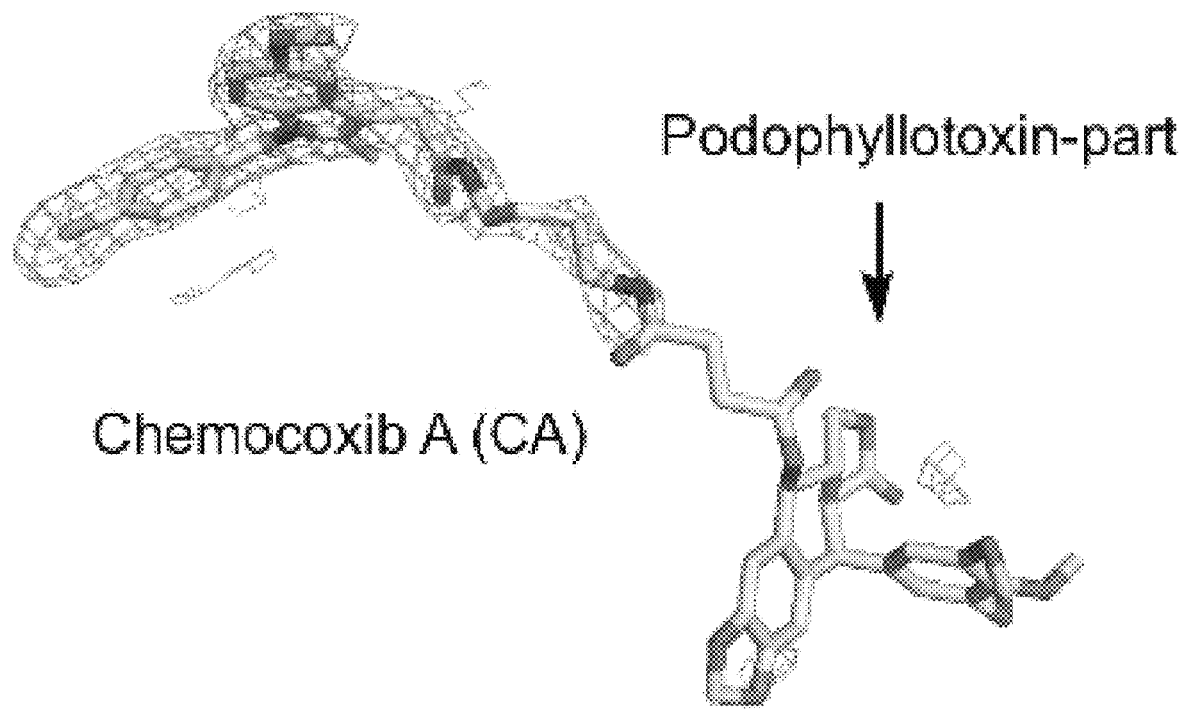
Figure 29E:
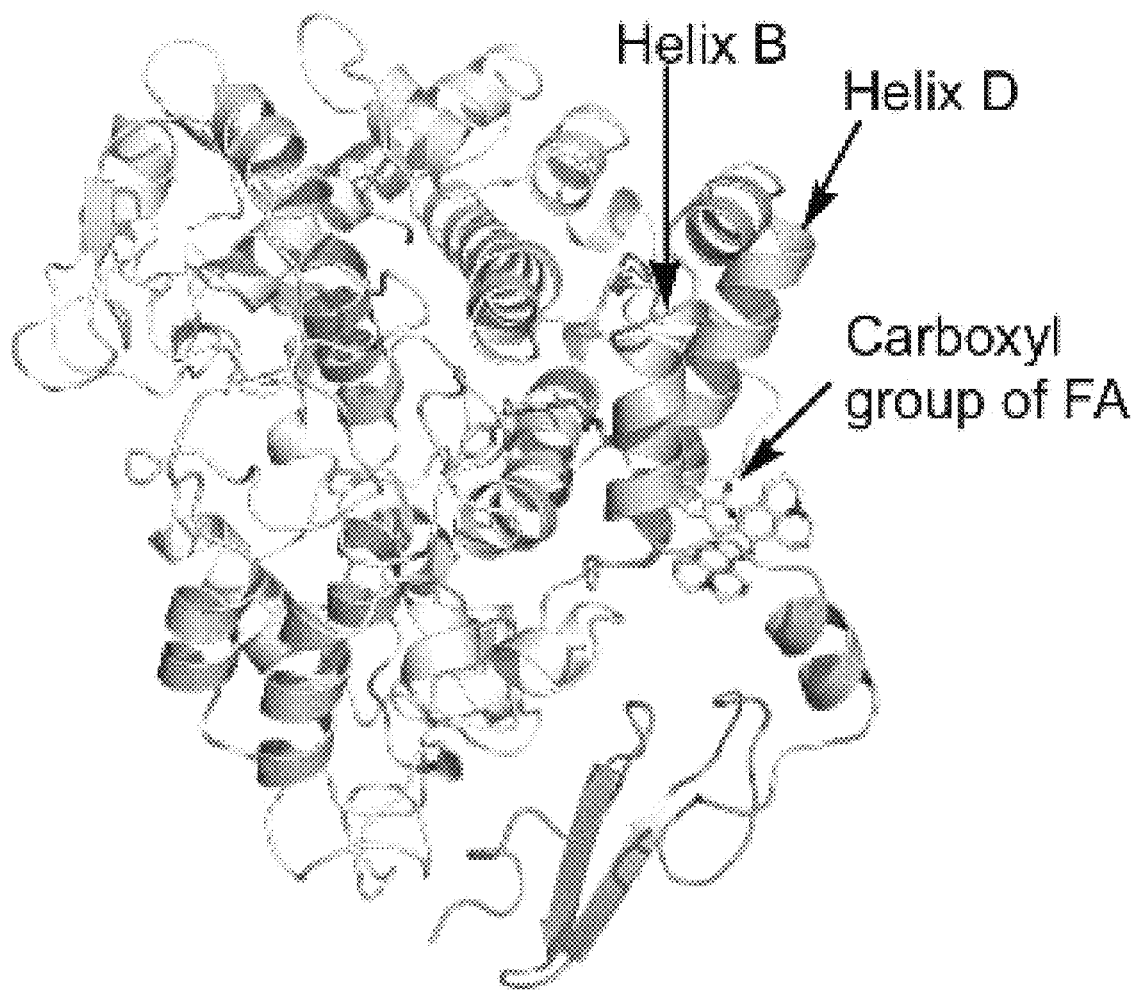
Figure 29F:
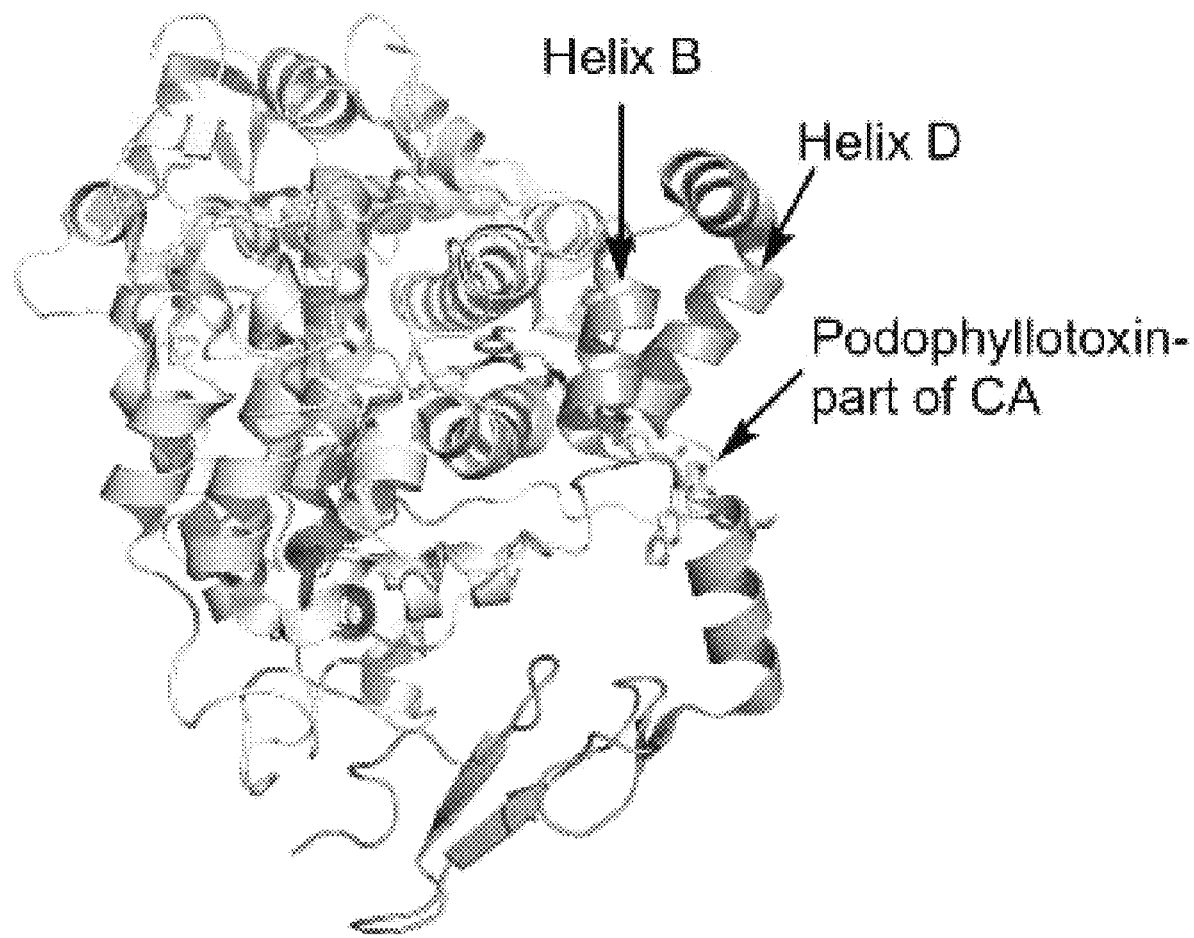

FIG. 28 shows schematic views illustrating chemical synthesis and optimization of fluorocoxib Q and chemocoxib A, according to an embodiment of the disclosure.

FIGS. 29A-F show images illustrating the structures, electron density, and binding of various structures according to an embodiment of the disclosure. (A) shows an image illustrating the structure of fluorocoxib A and B. (B) shows an image illustrating the structure of chemocoxib A. (C) shows an image illustrating an electron density map (Fo-Fc at 3σ) around fluorocoxib A. (D) shows an image illustrating an electron density map (Fo-Fc at 3σ) around chemocoxib A. (E) shows an image illustrating fluorocoxib A (stick) bound to COX-2 enzyme (ribbon). (F) shows an image illustrating chemocoxib A (stick) bound to COX-2 enzyme (ribbon).

Figure 30A:
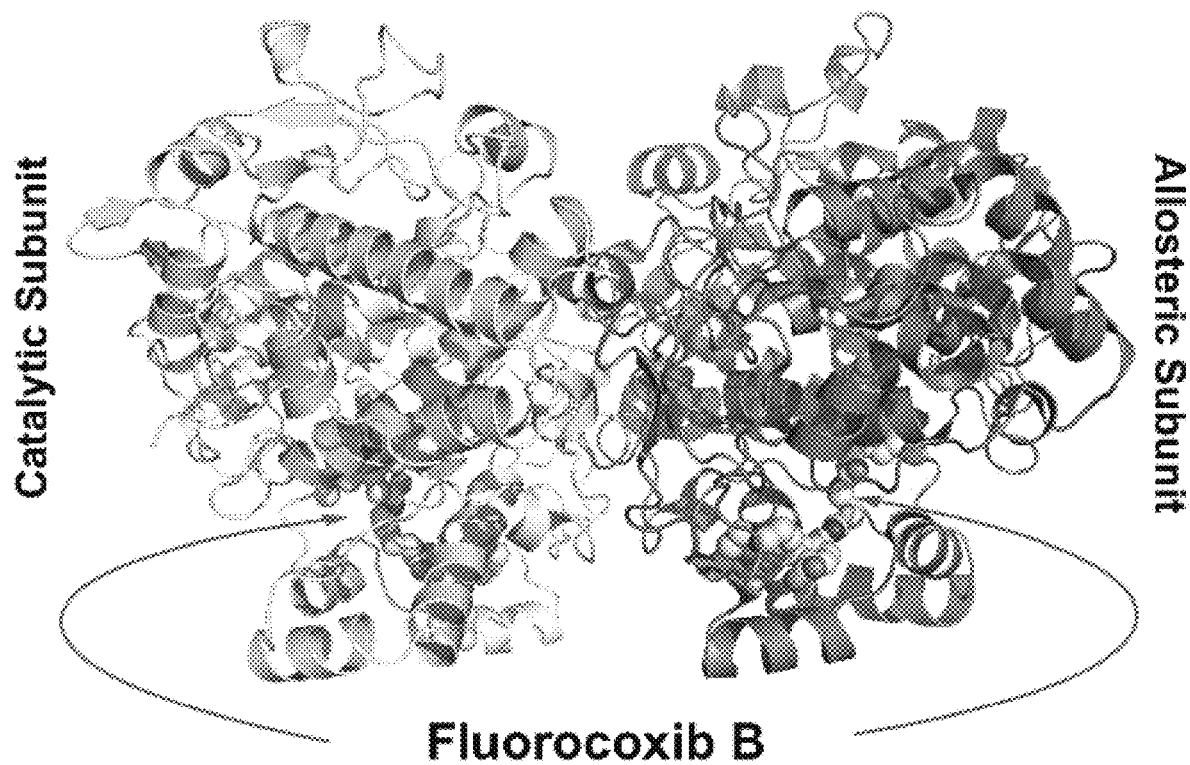
Figure 30B:
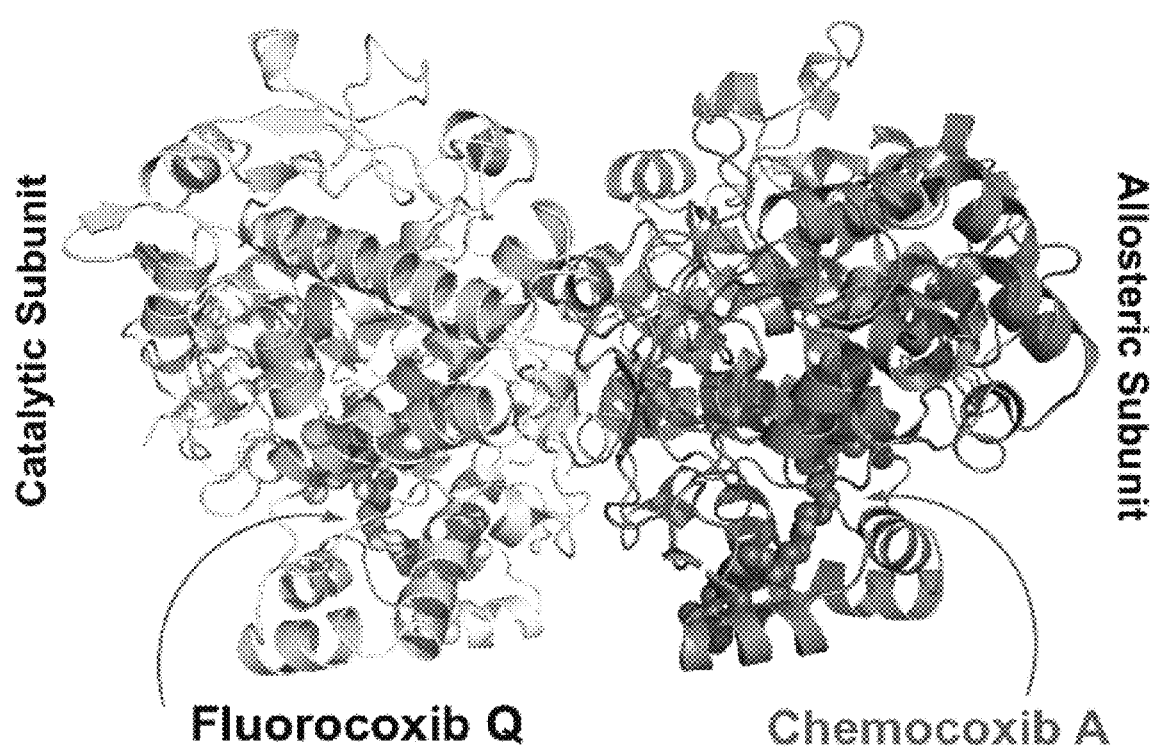

FIGS. 30A-B show images of various compounds bound to COX-2, according to an embodiment of the disclosure. (A) shows an image illustrating x-ray co-crystal structure of fluorocoxib B bound to COX-2 homodimers. (B) shows possible co-binding of fluorocoxib Q and chemocoxib A at COX-2 active sites. FQ may bind in catalytic subunit and CA at the allosteric subunit for inhibition.

Figure 31:
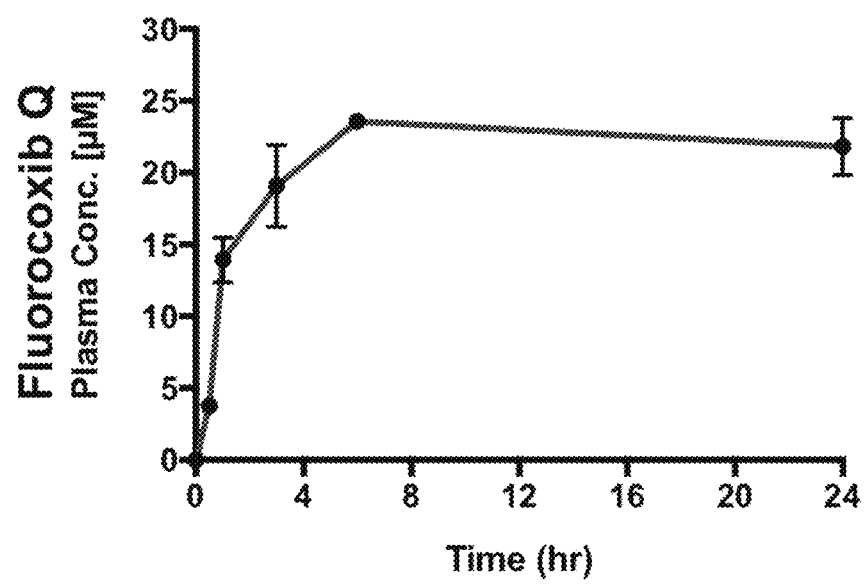

FIG. 31 shows a graph illustrating in vivo plasma concentration of fluorocoxib Q in CD-1 mice (10 mg/kg, i.p.).

FIGS. 32A-E show images and a graph illustrating imaging of mice with loaded and unloaded nanoparticles. (A) shows an image illustrating the chemical structure of fluorocoxib Q. (B) shows an image illustrating a micelle loaded with fluorocoxib Q and chemocoxib A. (C) shows images illustrating Athymic Balb/C nu/nu female mice bearing orthotopic breast cancer xenografts at the inguinal mammary fatpads that were injected with either un-loaded nanoparticles (left mouse, s.c.) or loaded chemocoxib A-fluorocoxib Q-nanoparticles (CA-FQ-NP) (right mouse, s.c.) and imaged in vivo at 49 hours post-injection on IVIS200. (D) shows an image illustrating ex vivo imaging of brain (B), muscle (M), tumor (T), liver (L), lung (Lu), and kidney (K) using IVIS 200 imaging system. (E) shows a graph illustrating quantification of photons/sec in ex vivo organs using ROI measurements (n=6).

DESCRIPTION OF EXEMPLARY EMBODIMENTS

The details of one or more embodiments of the presently-disclosed subject matter are set forth in this document. Modifications to embodiments described in this document, and other embodiments, will be evident to those of ordinary skill in the art after a study of the information provided in this document. The information provided in this document, and particularly the specific details of the described exemplary embodiments, is provided primarily for clearness of understanding and no unnecessary limitations are to be understood therefrom. In case of conflict, the specification of this document, including definitions, will control.

While the terms used herein are believed to be well understood by those of ordinary skill in the art, certain definitions are set forth to facilitate explanation of the presently-disclosed subject matter. Unless defined otherwise, all technical and scientific terms used herein have the same meaning as is commonly understood by one of skill in the art to which the invention(s) belong. All patents, patent applications, published applications and publications, GenBank sequences, databases, websites and other published materials referred to throughout the entire disclosure herein, unless noted otherwise, are incorporated by reference in their entirety. Where reference is made to a URL or other such identifier or address, it understood that such identifiers can change and particular information on the internet can come and go, but equivalent information can be found by searching the internet. Reference thereto evidences the availability and public dissemination of such information.

As used herein, the abbreviations for any protective groups, amino acids and other compounds, are, unless indicated otherwise, in accord with their common usage, recognized abbreviations, or the IUPAC-IUB Commission on Biochemical Nomenclature (see, Biochem. (1972) 11(9): 1726-1732).

Following long-standing patent law convention, the terms "a", "an", and "the" refer to "one or more" when used in this application, including the claims. Thus, for example, reference to "a cell" includes a plurality of such cells, and so forth.

Unless otherwise indicated, all numbers expressing quantities of ingredients, properties such as reaction conditions, and so forth used in the specification and claims are to be understood as being modified in all instances by the term "about". Accordingly, unless indicated to the contrary, the numerical parameters set forth in this specification and claims are approximations that can vary depending upon the desired properties sought to be obtained by the presently-disclosed subject matter.

As used herein, the term "about," when referring to a value or to an amount of mass, weight, time, volume, concentration or percentage is meant to encompass variations of in some embodiments±20%, in some embodiments±10%, in some embodiments±5%, in some embodiments±1%, in some embodiments±0.5%, and in some embodiments±0.1% from the specified amount, as such variations are appropriate to perform the disclosed method.

As used herein, ranges can be expressed as from "about" one particular value, and/or to "about" another particular value. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

Provided herein, in some embodiments, is a targeted fluorescent probe. In one embodiment, the probe includes the structure according to Formula I:

In another embodiment, the probe includes a 5-isomer or 6-isomer of the structure according to Formula I. In a further embodiment, R includes, but is not limited to, O⁻,

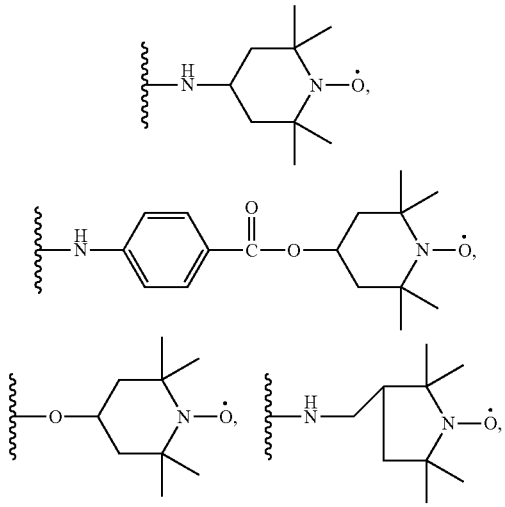

or any other suitable group for forming an activatable compound. Other suitable groups for forming an activatable compound include, but are not limited to, free radical binding group, groups that contain a hydrophobic and hydrophilic functionality, or a combination thereof. In certain embodiments, where R is O⁻, the 5-isomer forms fluorocoxib A and the 6-isomer forms fluorocoxib B; where R is

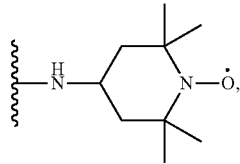

the 5-isomer forms fluorocoxib Q1 (also referred to herein as compound 1 or LM-9921) and the 6-isomer forms fluorocoxib Q2 (also referred to hererin as compound 2 LM-9923); where R is (I)

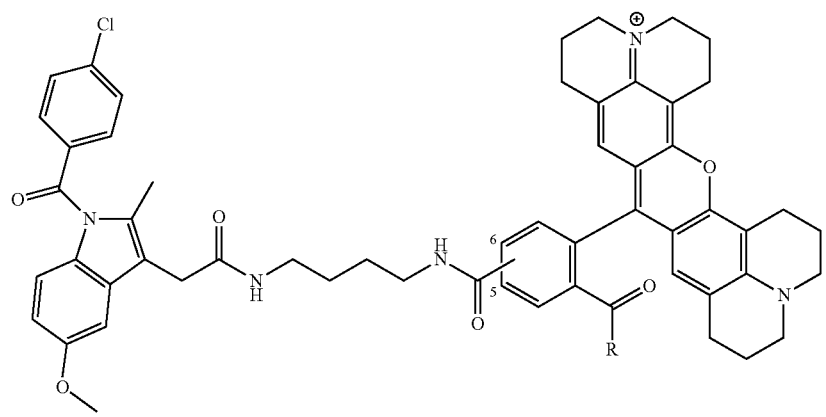

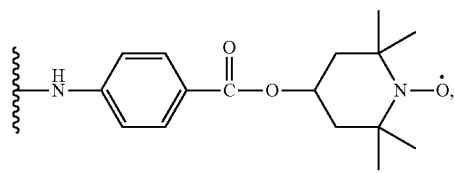

the 5-isomer forms fluorocoxib Q3 (also referred to herein as compound 3 or LM-9924); where R is

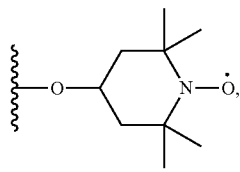

the 5-isomer forms fluorocoxib Q4 (also referred to herein as compound 4 or LM-9926); and where R is

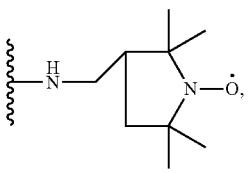

the 5-isomer forms fluorocoxib Q5 (also referred to herein as compound 5).

The compounds according to Formula I are cyclooxygenase-2 (COX-2)-targeted fluorescent probes which are selectively taken up by COX-2 positive cells. In some embodiments, the compounds, such as fluorocoxib Q1-Q5, are nitroxide derivatives of a carboxy-X rhodamine (ROX) fluorophore, where any suitable nitroxide moiety is linked to the ROX fluorophore. Suitable nitroxide moieties include, but are not limited to, TEMPO or PROXYL nitroxide moieties. These nitroxide moieties may be linked to the ROX fluorophore through any suitable linker, such as, but not limited to, nitrogen, oxygen, silicon, or sulfer.

In some embodiments, the nitroxide moieties quench the fluorescence of the ROX fluorophore in an excited electronic state, such that the nitroxide derivatives are non-fluorescent or exhibit reduced fluorescence as compared to ROX fluorophores when in the excited state. In one embodiment, the nitroxide moieties are also reactive with free radicals. In another embodiment, upon reaction with such free radicals, these nitroxide derivatives of ROX fluorophores are activated to provide fluorescent emission and/or enhanced fluorescent emission. Accordingly, in certain embodiments, the nitroxide derivatives, such as fluorocoxib Q1-Q5, form activatable pro-fluorescent probes which are both targeted to COX-2 and provide increased/enhanced fluorescence upon reaction with free radicals. Furthermore, in some embodiments, additional functionalities may be added on the free carboxyl group of the fluorophore without altering the COX-2 binding affinity.

Although discussed herein primarily with regard to nitroxide derivatives of ROX fluorophores, as will be appreciated by those skilled in the art the disclosure is not so limited and may include any other suitable fluorophore. Other suitable fluorophores include, but are not limited to, other fluorescent compounds containing a free carboxylic acid group. For example, in one embodiment, the fluorophores include near infrared dyes containing a free carboxylic acid group. When these other fluorophores are linked to one or more of the nitroxide moieties disclosed herein, they form activatable nitroxide derivatives thereof. Accordingly, in another embodiment, the color (emission wavelength) of the compounds disclosed herein may be selected and/or changed by choosing different fluorophores to link with the nitroxide moieties. In a further embodiment, the threshold of the fluorescence may be precisely tuned.

Due to the activatable fluorescence discussed above, in some embodiments, the nitroxide derivatives provide an increased signal-to-noise ratio as compared to non-activatable compounds. For example, in contrast to fluorocoxib A and fluorocoxib B, which always fluoresce (i.e., are non-activatable) and thus are hampered by strong noise from non-targeted normal tissues/organs due to distribution and/or inefficient clearance of probes, the nitroxide derivatives only become fluorescent at the target site and not at the non-targeted normal tissue/organ sites, which decreases or eliminates background noise. Stated another way, in some embodiments, the compounds disclosed herein provide background-free targeted imaging.

In some embodiments, the compounds disclosed herein provide targeted fluorescence and/or detection of specific cells/diseases states. For example, in inflammation and/or various cancers the cells express COX-2 at high levels. The COX-2 targeted compounds disclosed herein are selectively taken up by these COX-2 expressing cells (e.g., COX-2 targeted fluorescent probes displayed a high degree of selectivity of uptake in COX-2 positive tumors as compared to COX-2 negative tumors). Additionally or alternatively, in inflammation and/or various cancers the cells produce superoxide, a reactive oxygen species that is a significant contributor to cellular levels of oxidative stress, which results in cellular damage due to the generation of peroxides and free radicals. In such embodiments, after selective uptake by the COX-2 expressing cells, the compounds disclosed herein are activated by trapping and/or reacting with the free radicals. This selective uptake and subsequence activation provides background-free targeted imaging in vitro or in vivo and/or precise detection of cancers, inflammation, and/or other disease states associated with free radicals. In certain embodiments, this precise detection and imaging is provided with accurate surgical margins.

Accordingly, also provided herein, in some embodiments, is a method of detecting a disease in a subject. In one embodiment, the method includes administering one or more of the compounds disclosed herein to a subject and then imaging the subject. The administration may be by any suitable method, including, but not limited to, intraperitoneal, intravenously, or any other suitable method. In another embodiment, administration of the one or more compounds disclosed herein provides target-specific delivery of quenched agents into COX-2 expressing cells and subsequent on-site fluorescence activation by radical reduction allowing selective visualization these cells in vivo. For example, upon radical reduction in cancer cells, the COX-2-targeted probes provide enhanced fluorescent emission for in vivo detection of COX-2 expressing tumors. Although discussed above with regard to tumors, as will be appreciated by those skilled in the art, the disclosure is not so limited and may include any other disease characterized by COX-2 expressing cells, such as inflammation and/or cancer (e.g., colon cancer, skin cancer, gastrointestinal (GI) cancer, or bladder cancer). Therefore, this technology can be widely adapted for background free detection of inflammatory and neoplastic diseases in preclinical and clinical settings.

Additionally or alternatively, in some embodiments, the compounds disclosed herein may be co-delivered with one or more therapeutic agents. Suitable therapeutic agents include, but are not limited to, cytotoxic agents, antitumor agents, targeted agents, co-targeted agents (i.e., therapeutic agents with the same target as the activatable compound), or any other therapeutic agent that may be co-delivered with the activatable compounds disclosed herein. For example, in one embodiment, one or more of the activatable compounds disclosed herein (e.g., fluorocoxib Q1-Q5) may be co-delivered with chemocoxib A, a COX-2 targeted cytotoxic antitumor agent. In another embodiment, the activatable compound and the therapeutic agent are co-loaded into a nanoparticle. The nanoparticle in which the activatable compounds and the therapeutic agent are co-loaded includes any suitable nanoparticle, such as, but not limited to, an ROS-responsive micellar nanoparticle, a di-block polymer derived micellar nanoparticle, or a combination thereof.

Once in the presence of ROS, such as in tumor cells, the nanoparticles disassemble to co-release both the activatable compound and the therapeutic agent. In certain embodiments, upon release, the activatable compound and/or the therapeutic agent bind with intracellular COX-2, where the activatable compounds become fluorescently activated by ROS to provide visualization of delivery of the therapeutic agent in real-time.

Further provided herein, in some embodiments, is a method of forming activatable compounds. In some embodiment, the method includes providing a fluorophore with a carboxylic acid group, converting the carboxylic acid group into an anhydride using ethyl chloroformate, and then reacting the anhydride containing fluorophore with an amino-, amino-methyl-, or hydroxyl-nitroxide radical to form the nitroxide derivative. For example, in one embodiment, the method includes providing a carboxy-X rhodamine (ROX) fluorophore, converting the carboxylic acid group thereof into an anhydride using ethyl chloroformate, and then reacting the resulting anhydride containing fluorophore with an amino-TEMPO, amino-methyl-PROXYL, or hydroxy-TEMPO radical to form the desired conjugates.

Although any methods, devices, and materials similar or equivalent to those described herein can be used in the practice or testing of the presently-disclosed subject matter, representative methods, devices, and materials are described herein.

EXAMPLES

The presently-disclosed subject matter is further illustrated by the following specific but non-limiting examples. The examples may include compilations of data that are representative of data gathered at various times during the course of development and experimentation related to the instant disclosure.

Example 1—Synthesis of a Selective, Activatable Imaging Probe

Introduction

Selective visualization of cancer cells shows enormous promise for effective diagnosis and treatment of carcinogenesis. However, currently available imaging probes are limited in their ability to detect target tissues selectively because of low target-to-background specificity. Generally, targeted imaging probes show lack of specificity due to probe penetration, retention, and inefficient clearance from non-targeted sites.

Figure 1:
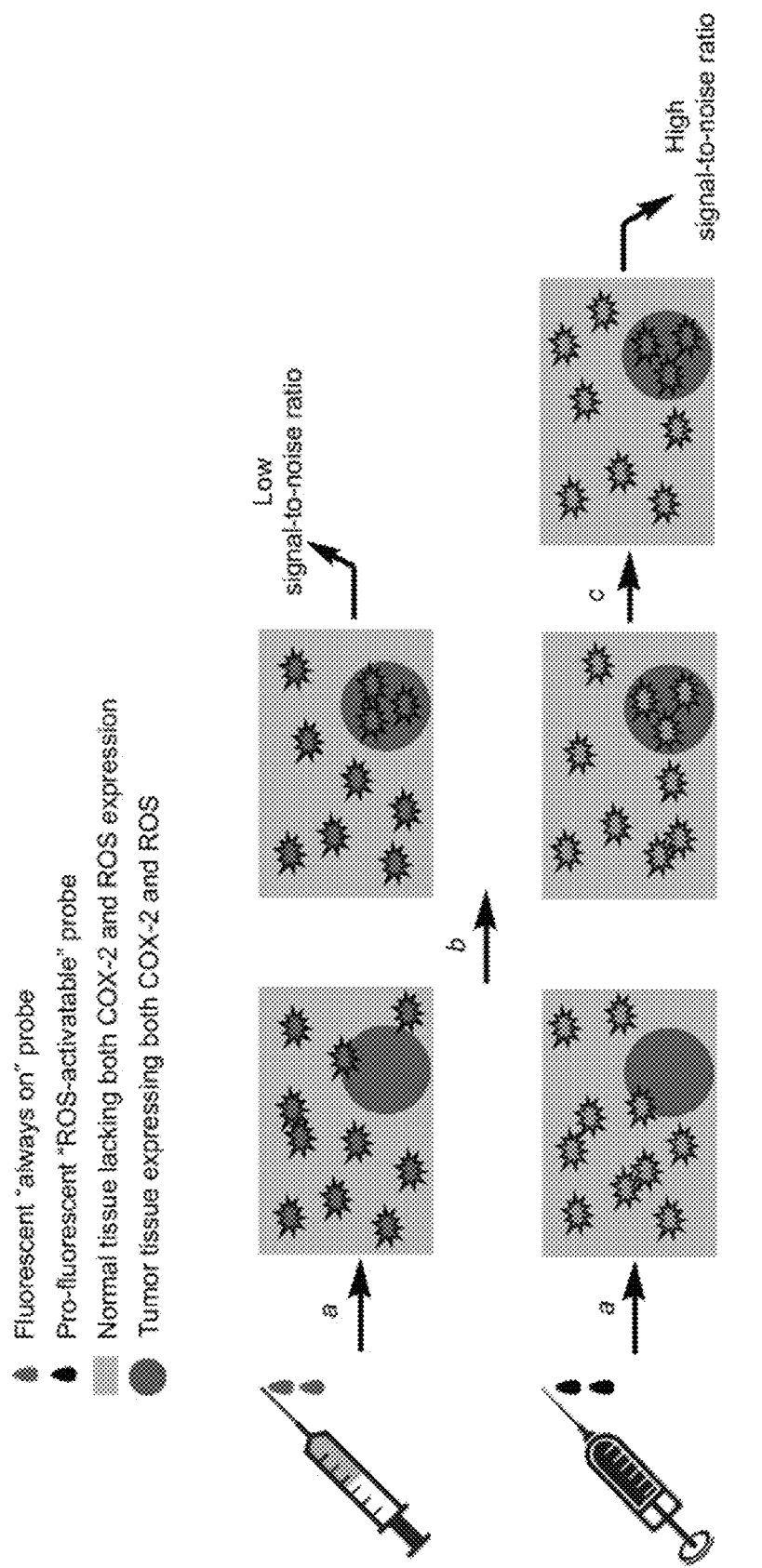
FIG. 1 shows a schematic view illustrating imaging with existing probes and activatable probes according to an embodiment of the disclosure.

As an imaging target, COX-2 is particularly attractive because it is an inducible enzyme that is expressed in inflammation and various cancers at high levels. In view thereof, the instant inventors have developed the first cyclooxygenase-2 (COX-2)-targeted fluorescent probe, Fluorocoxib A. This COX-2 targeted fluorescent probe displayed a high degree of selectivity of uptake in the COX-2 positive tumors as compared to COX-2 negative tumors, and provided selective visualization of COX-2 in inflammation and cancer. Having an established proof-of-concept compound for COX-2-targeted imaging, the instant inventors next sought to expand the applicability of this approach by designing activatable pro-fluorescent nitroxide probes that are capable of visualization of cancer with high signal-to-noise ratios (FIG. 1).

In addition to forming a portion of the activatable pro-fluorescent probes, nitroxides are also effective small molecule antioxidants in biological systems due to their broad distribution and ability to react with and detoxify harmful free radicals. Superoxide, one of the main reactive oxygen species produced in the cell, is a significant contributor to cellular levels of oxidative stress, which results in cellular damage due to the generation of peroxides and free radicals and has been implicated primarily in initiation and progression of neoplastic diseases. Nitroxides have shown significant potential as small molecule antioxidants in mammalian cells due to their broad distribution and ability to react and detoxify harmful free radicals.

Figure 2:
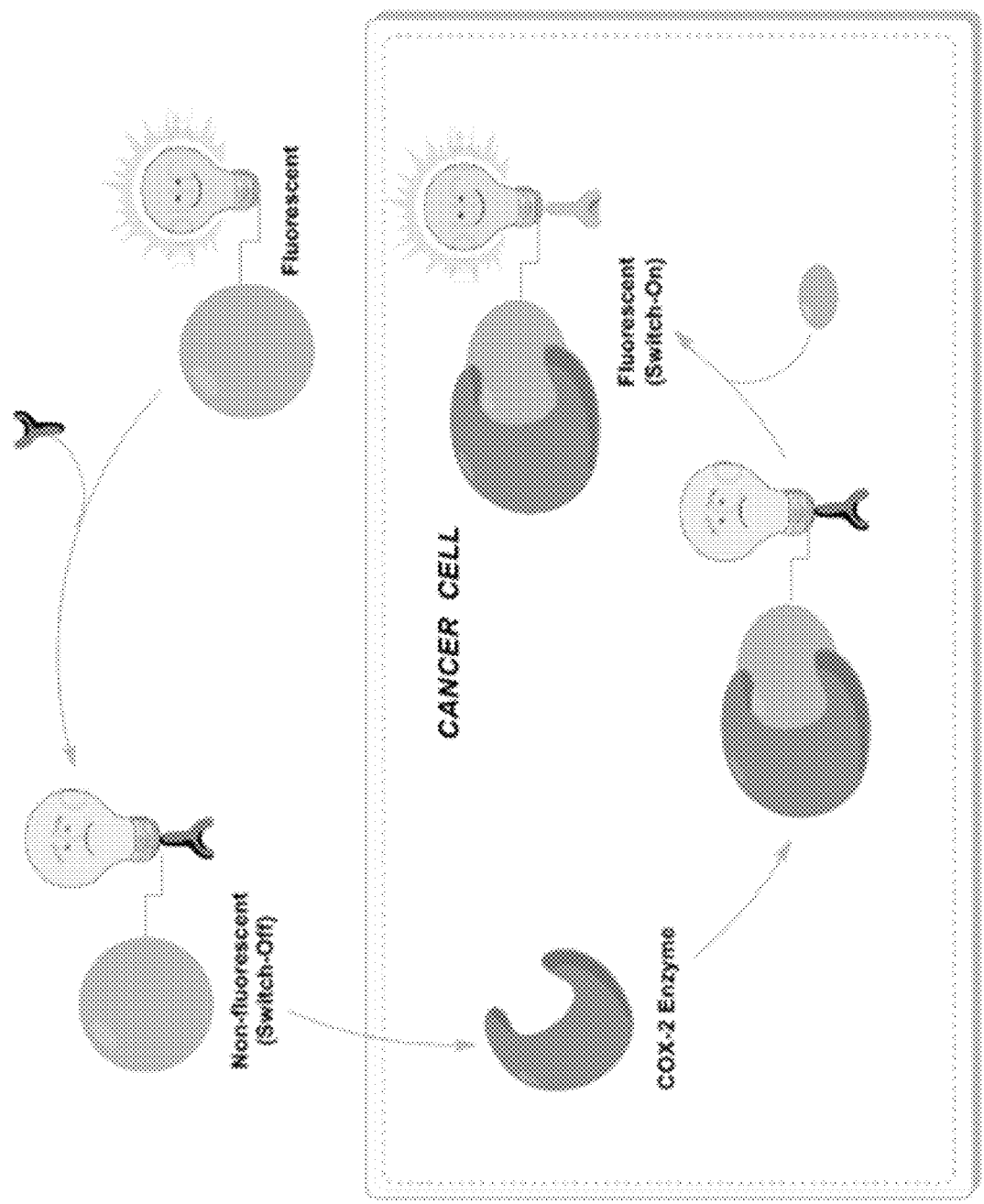
FIG. 2 shows a schematic view illustrating activation of a probe according to an embodiment of the disclosure.
Figure 3:
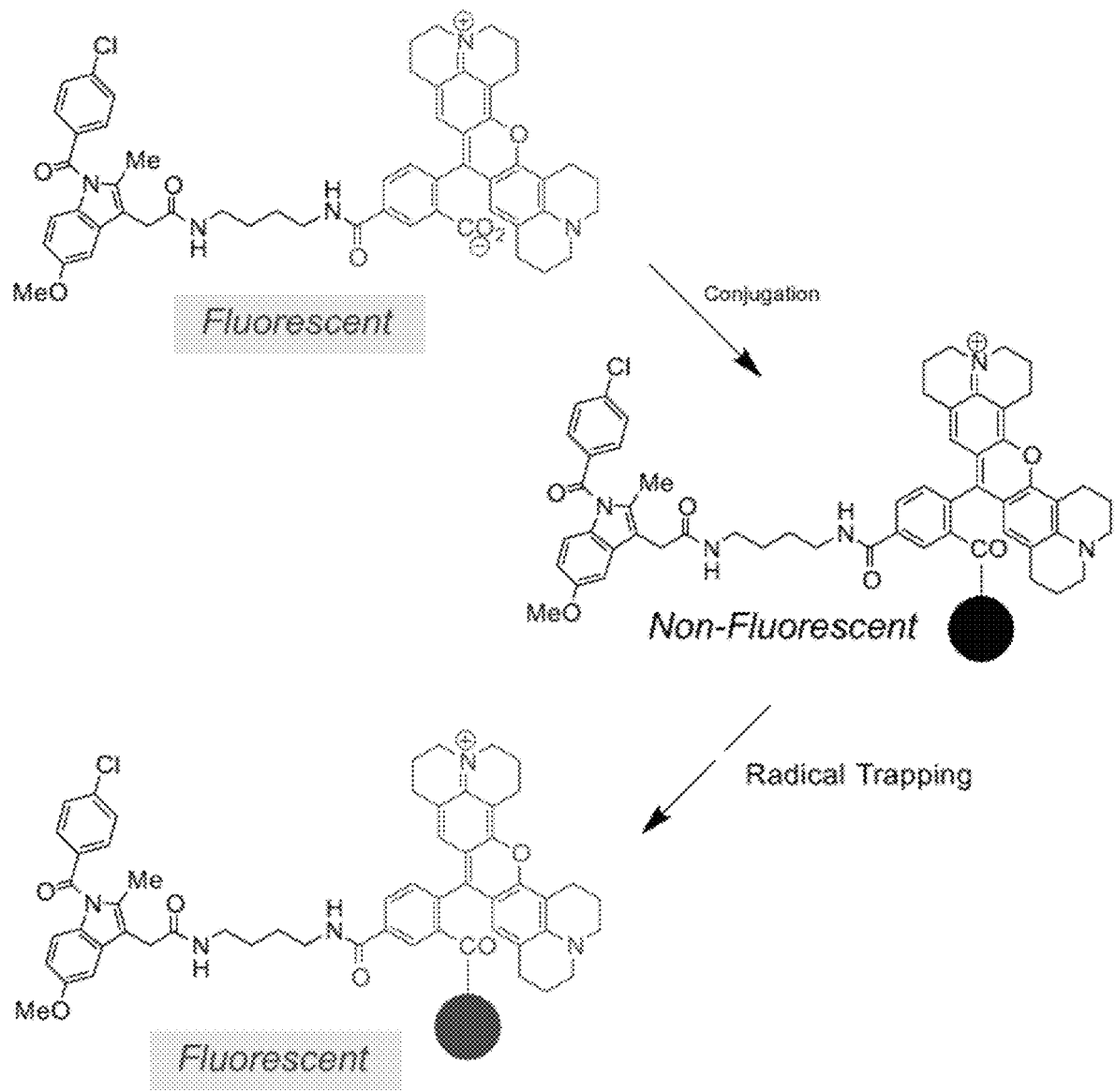
FIG. 3 shows a schematic view illustrating design of quenched probes according to an embodiment of the disclosure.

This Example describes the synthesis, characterization, and evaluation of a series of nitroxide derivatives of fluorocoxib A and B. These nitroxide derivatives contain a carboxy-X-rhodamine (ROX) fluorophore closely linked to a TEMPO or PROXYL nitroxide moiety to form COX-2 targeted activatable profluorescent nitroxide probes. These probes exhibited selective COX-2 inhibition in purified enzymes and intact cells, and showed significantly reduced fluorescence due to efficient quenching of the excited electronic state of the fluorophore by the nitroxide radical. Upon radical trapping in cancer cells, these COX-2-targeted probes demonstrated enhanced fluorescent emission (i.e., fluorescent activation), making them effective in detecting COX-2 in tissue culture and in vivo tumor models. This resulted in high signal-to-noise ratio and significant improvement in tumor visualization over currently available techniques. Thus, this novel strategy provides target-specific delivery of quenched agents into tumor cells and subsequent on-site fluorescence activation by radical trapping for selective visualization of tumor in vivo (FIGS. 2-3). This technology is also widely adaptable for background free detection of inflammatory and neoplastic diseases in preclinical and clinical settings.

Results and Discussion

Development of a Tunable and Activatable Pro-Fluorescent Probe

Carboxy-X-rhodamines are well known to show strong emission of wavelengths over 600 nm, and their fluorescence is unaffected by solvent polarity and pH ranged from 4 to 10. Furthermore, these dyes are relatively resistant to photobleaching, because they contain added structural rigidity from multiple n-propylene bridging, which prevents fluorescence deactivation by non-radiative processes.

Cancer cells are distinct from normal cells primarily because of they contain free radicals. This is due to their high oxidative stress. As such, a probe that becomes activated in such an environment yields a highly tumor-specific signal with greatly reduced background noise. For the development of activatable probes, nitroxides such as TEMPO and PROXYL radicals were used, which quench fluorescence of certain rhodamine-type fluorophores. Although the quenching mechanism is still not quite clear, the triplet quenching of TEMPO or PROXYL is interpreted by two different quenching mechanism, (i) triplet-doublet energy transfer, and (ii) enhanced intersystem crossing. In the enhanced intersystem crossing mechanism, radicals act as a catalyst for intersystem crossing from the triplet to the ground state.

Therefore, to develop sensitive pro-fluorescence probes suitable to reach protein targets in cancer cells, rhodamine-based COX-2 probes, such as fluorocoxibs which contain a free carboxylic acid group that is conjugable with TEMPO or PROXYL quenching templates, were used. As with all nitroxide radicals, the pro-fluorescent rhodamine-containing nitroxide radicals are sensitive to another radical. TEMPO and PROXYL are stable radical species. In radical rich environments they react with them and lose their fluorescence quenching ability allowing the fluorophore to become fluorescent again. Using these unique physicochemical properties of nitroxide radicals, we developed a series of acidic sensitive fluorescence probes targeted to COX-2.

Figure 4:
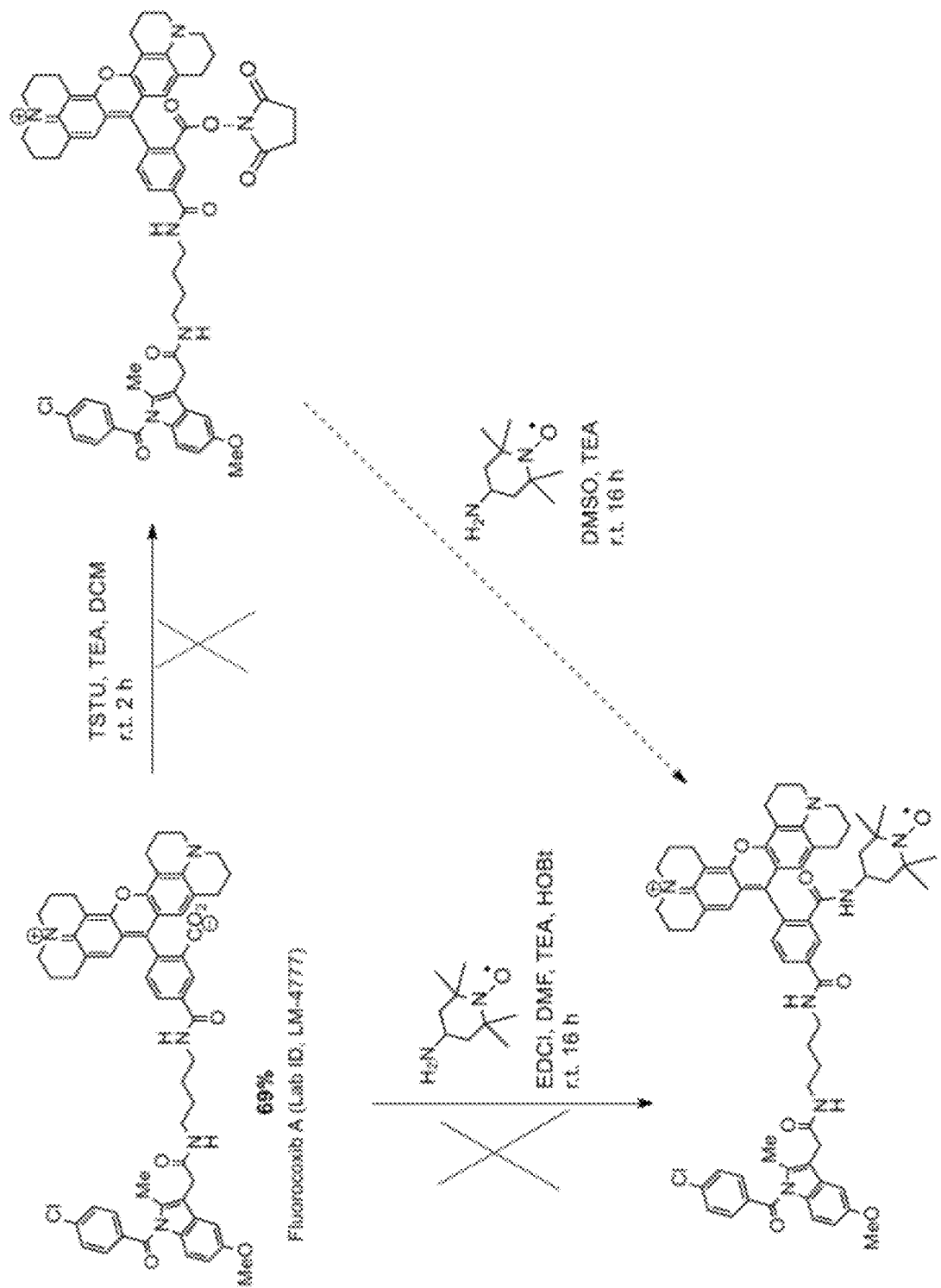
FIG. 4 shows a schematic view illustrating various attempts at synthesizing activatable probes according to an embodiment of the disclosure.
Figure 5:
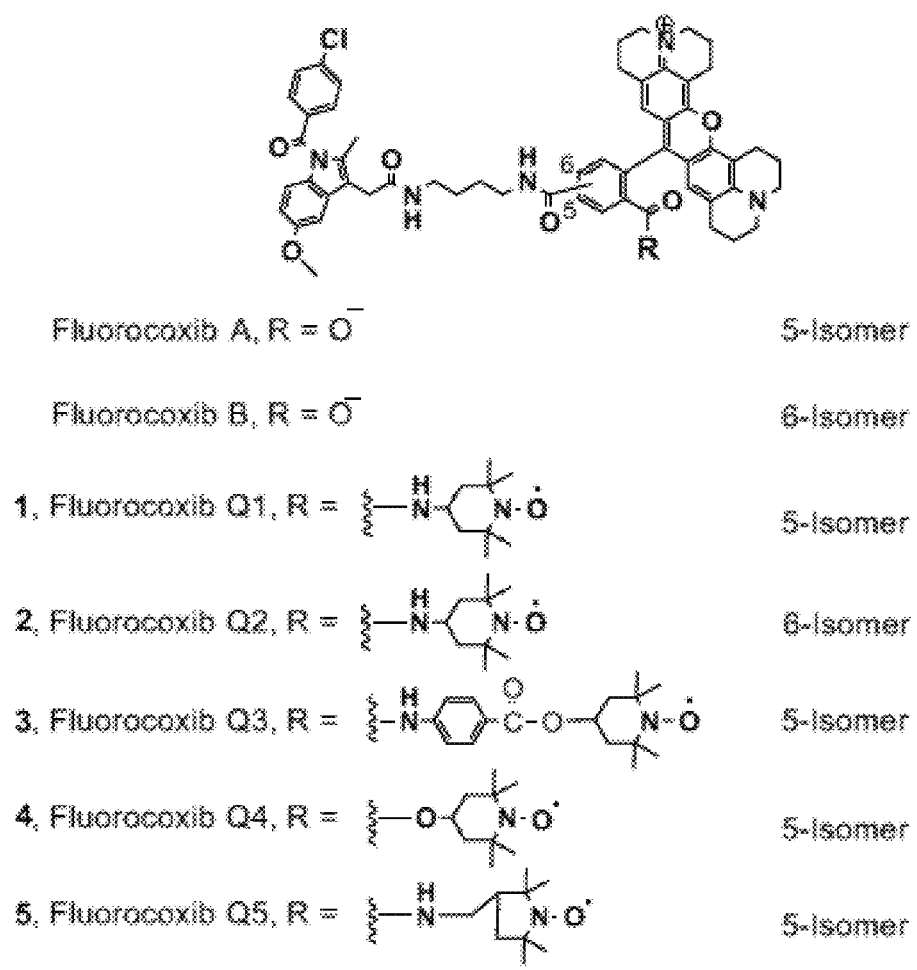
FIG. 5 shows a chart illustrating the structure of various activatable probes according to an embodiment of the disclosure.
Figure 6:
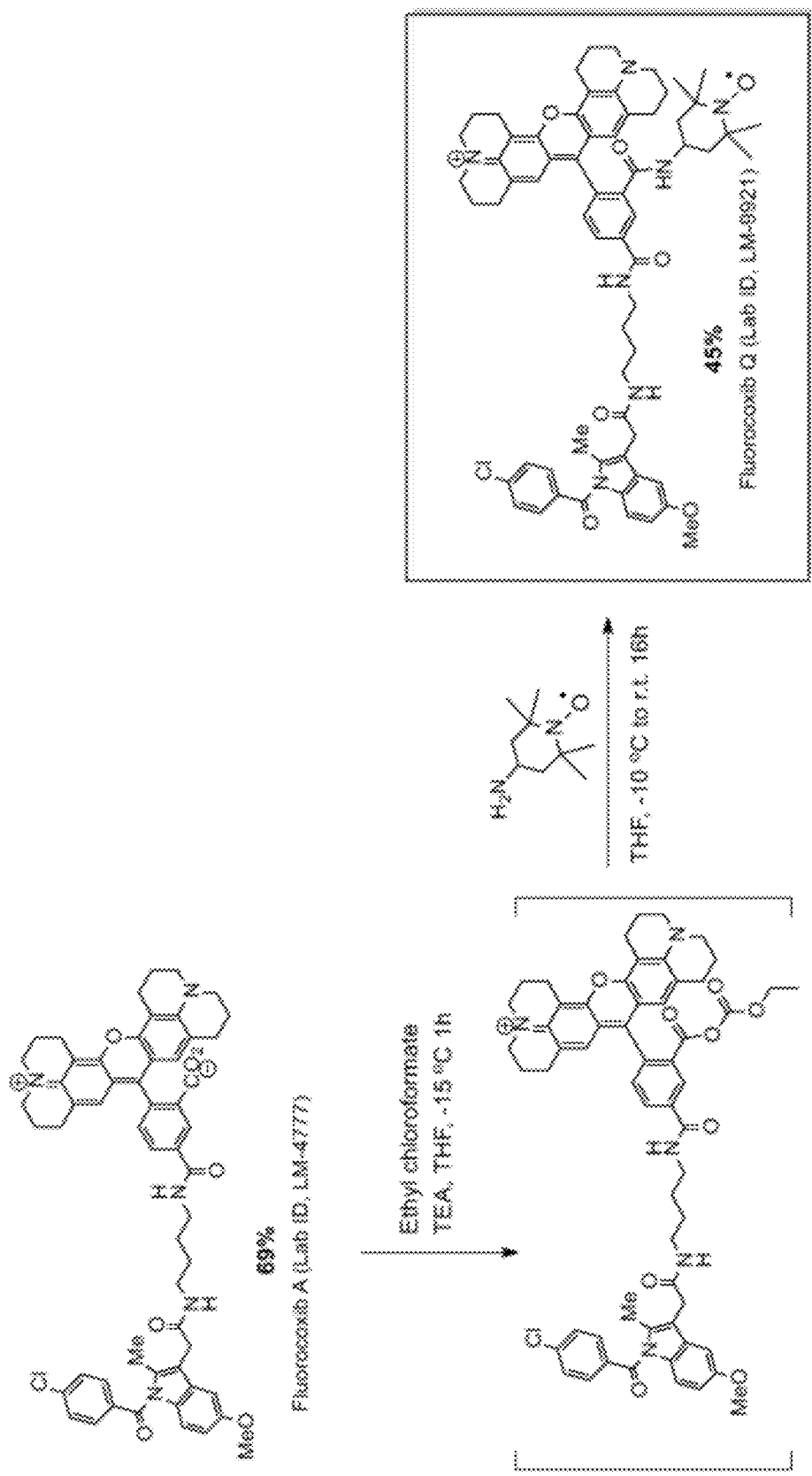
FIG. 6 shows a schematic view illustrating synthesis of fluorocoxib Q1, according to an embodiment of the disclosure.

Initially, fluorocoxib A and fluorocoxib B containing a free carboxylic acid group onto rhodamine moiety of the molecule were synthesized. The instant inventors then attempted a carbodiimide coupling strategy to form an amide or ester of the carboxyxlic acid group, in order to synthesize TEMPO-fluorocoxib conjugates. Unfortunately, no amide or ester was isolated from this coupling reaction. Next, the instant inventors attempted to activate the carboxylic acid using N,N,N',N'-tetramethyl-O—(N-succinimidyl) uronium tetrafluoroborate (TSTU), which also failed to activate the carboxilic acid group. Without wishing to be bound by theory, it is believed that this was due to steric hindrance. Therefore, to overcome this problem, the instant inventors converted the carboxylic acid into an anhydride using ethyl chloroformate, which was then reacted with amino-TEMPO, aminomethyl-PROXYL, or hydroxy-TEMPO radicals to afford the desired conjugates (FIG. 4). Using this synthetic protocol, as a general method, a series of TEMPO and PROXYL analogs tethered to fluorocoxib A or B analogs (1-5) were synthesized (FIGS. 5-12).

Radical-Dependent Fluorescence Activation

The TEMPO- and PROXYL-fluorocoxib probes are non-fluorescent ($\Phi_{fl}$<0.3) in their non-trapped form, whereas fluorocoxib A or B are highly fluorescent ($\Phi_{fl}$<0.9) (FIG. 13). However, the absorbance and fluorescence of the TEMPO- and PROXYL-fluorocoxib probes increases in a time-dependent fashion when incubated in a DMSO/EtOH solution (FIGS. 14-15). Referring to FIG. 15, it is noted that at about 16 hours, fluorescence (ex 586 nm) read about 120,000 cps at 607 nm. Turning to FIG. 16, as compared to 5-ROX acid, which had extinction of 36/mM/cm at 580 nm and quantum yield of 0.94 at 604 nm, and fluorocoxib A, which had extinction of 45/mM/cm at 579 nm and quantum yield of 0.93 at 602 nm, fluorocoxib Q1 had extinction of less than 0.4/mM/cm at 586 nm and quantum yield of less than 0.36 at 607 nm. Without wishing to be bound by theory, it is believed that the time-dependent increase in fluorescence and measured fluorescence at 607 nm is the result of reduction/oxidation of fluorocoxib Q1 in the DMSO/EtOH solution (FIG. 16).

In physiological conditions, ascorbic acid loses an electron to form a radical and then with loss of a second electron to form dehydroascorbic acid. However, if there a second radical present in the system, such as a nitroxide radical, it is typically trapped by the second radical and becomes a stable compound. In view thereof, the fluorescent activation of the instant nitroxide derivatives was also evaluated utilizing these unique properties of ascorbic acid. More specifically, probe 1 was incubated with ascorbic acid, where a time-dependent increase of fluorescence was observed (FIG. 17). The fluorescence emission was measured fluorometrically. Concentration dependent fluorescence increases were observed ascorbic acid concentration was increased from 10-, 100-, 1000-folds (FIG. 18).

Evaluation of Activatable Probes as COX-2 Specific Inhibitors in Purified Protien and Intact Cells The in vitro cyclooxygenase (ovine COX-1 or human COX-2) inhibitory activities of these probes were tested by a previously described TLC assay (FIGS. 19-21). Briefly, reaction mixtures of 200 μL consisted of hematin-reconstituted protein in 100 mM Tris-HCl, pH 8.0, 500 μM phenol, and [1-$^{14}$C]arachidonic acid (50 μM, about 55-57 mCi/mmol, Perkin Elmer). The IC$_{50}$ values for the inhibition of purified COX enzymes by test compounds are listed in Table 1. Compounds 1 and 2 displayed selective COX-2 inhibition (Table 1). Compound 3, a conjugate of fluorocoxib A and TEMPO tethered through a fenamate linker, also displayed selective COX-2 inhibition. Compounds 4 and 5 also inhibited COX-2 selectively, although with less potency. This structure-activity relationship (SAR) study identified compound 1 as the most potent and selective COX-2 inhibitor in the series with an IC$_{50}$ value of 0.30 μM.

TABLE 1

In Vitro COX-1 and COX-2 isozyme inhibition assay data.

| Probe Nos. | oCOX-1 IC$_{50}$ (μM)$^a$ | mCOX-2 IC$_{50}$ (μM)$^a$ | COX-2 Selectivity Index$^b$ |
|---|---|---|---|
| 1 | >25 | 0.30 | >83 |
| 2 | >25 | 0.33 | >75 |
| 3 | >25 | 0.46 | >54 |
| 4 | >25 | 1.24 | >20 |
| 5 | >25 | 1.80 | >13 |
| Fluorocoxib A | >25 | 0.70 | >35 |
| Fluorocoxib B | >25 | 0.80 | >31 |

$^a$IC$_{50}$ values were determined by incubating several concentrations of inhibitors in DMSO with purified murine COX-2 (63 nM) and ovine COX-1 (22.5 nM) for 20 min followed by treatment with 1-$^{14}$C-AA (50 μM) at 37° C. for 30 s. Assays were run in duplicates.
$^b$In vitro COX-2 selectivity index (COX-1 IC$_{50}$/COX-2 IC$_{50}$)

Following the promising results from the purified enzyme assay, the ability of compound 1 to inhibit COX-2 in intact cells was examined using a previously reported method. 1483 human head and neck squamous cell carcinoma (1483

HNSCC) cells that express high levels of COX-2 were selected. These cells were treated with compound 1 dissolved in DMSO (0-5 µM, final concentration) for 30 min at 37° C. followed by the addition of [1-$^{14}$C]-arachidonic acid [10 µM, about 55 mCi/mmol, Perkin Elmer] for 20 min at 37° C. In this assay, compound 1 was identified as a potent COX-2 inhibitor with an IC$_{50}$ value of 0.28 µM (FIG. 22). Thus, these results suggest that conjugation of a nitroxide moiety onto fluorocoxibs allow these probes to retain the inhibitory potency and selectivity of the parent fluorocoxibs. This also suggests that they bind with COX-2 isozyme in a similar fashion as their parent fluorocoxibs.

Imaging of COX-2-Positive 1483 Cells and Tumors with Activatable Probes

To test the specific activation of probes in cancer cells, compound 1 was incubated at selected time points (0.5, 1.0, 2.0, 3.0 h). After washout, the cells were imaged under fluorescence microscope. At 0.5-1 h preincubation, there was no significant intracellular fluorescence observed. However, at 2-3 h preincubation, bright fluorescence appeared inside the cells, suggesting the activation occurred in the cancer cells (FIG. 23). In contrast, fluorocoxib A exhibited bright fluorescence at 0.5 h preincubation (FIG. 24).

The specificity of probe 1 was also evaluated by targeting COX-2 in human tumor xenografts. Nude mice bearing 1483 xenograft tumors on the left flank were dosed by intraperitoneal injection with 1 mg/kg fluorocoxib A or compound 1 (FIG. 25). At 3 h post-injection, fluorescence was observed in the tumor of mice dosed with fluorocoxib A (FIG. 26A) while no fluorescence was observed in the tumor of mice dosed with compound 1 (FIG. 26B). However, signal was detected in the COX-2 expressing 1483 tumors of mice dosed with compound 1 starting at 24 h. Maximum fluorescence is detectable in the tumor at 48 h post-injection of probe 1 (FIGS. 27A-C).

The discussion above shows that probe 1 is COX-2-targeted, non-fluorescent, and becomes highly fluorescent when reacted with free radicals present in cancer cells. This high sensitivity and target specific activation allows selective detection of cancer in vivo. Unlike other activatable probes, probe 1 consists of two independently functioning components, a targeted molecule and a free radical sensitive small-molecule fluorescence probe that is tunable and activatable. Therefore, this tool may be employed for a range of cancer types expressing COX-2. In addition, this technology allows not only the threshold of the fluorescence to be precisely tuned, but also the color (emission wavelength) can be changed by choosing different fluorophores, such as near infrared dyes containing a free carboxylic acid group.

Methods

Chemistry. Standard methods were utilized for the synthesis of fluorescent and non-fluorescent quenched probes.

Fluorometry. Steady state fluorescence excitation and emission spectra were determined for each compound with a Spex 1681 Fluorolog spectrofluorometer, equipped with a 450 W xenon arc lamp. The excitation and emission monochromator slit widths were 1-2 The solvent used was pH 7 buffer.

Inhibition Assay Using Purified COX-1 and COX-2. Inhibition of purified ovine COX-1 or mouse COX-2 by test compounds was assayed by a previously described method, which quantifies the conversion of [1-$^{14}$C]arachidonic acid to [1-$^{14}$C]prostaglandin products. Reaction mixtures of 200 ∝L consisted of hematin-reconstituted protein in 100 mM Tris-HCl, pH 8.0, 500 µM phenol, and [1-$^{14}$C]arachidonic acid (50 µM, ~55-57 mCi/mmol, Perkin Elmer). For the time-dependent inhibition assay, hematin-reconstituted COX-1 (44 nM) or COX-2 (66 nM) was preincubated at 25° C. for 17 min and 37° C. for 3 min with varying inhibitor concentrations in dimethylsulfoxide followed by the addition of [1-$^{14}$C]arachidonic acid (50 µM) for 30 s at 37° C. Reactions were terminated by solvent extraction in diethyl ether:methanol:1 M citrate buffer, pH 4.0 (30:4:1). The phases were separated by centrifugation at 2000 g for 2 min, and the organic phase was spotted on a thin-layer chromatography plate (EMD Kieselgel 60, VWR). The plate was developed in ethyl acetate:methylene chloride:glacial AcOH (75:25:1) at 4° C. Radiolabeled products were quantified with a radioactivity scanner (Bioscan, Inc., Washington, D.C.). The percentage of total products observed at different inhibitor concentrations was divided by the percentage of products observed for protein samples preincubated for the same time with dimethyl sulfoxide.

Cell Culture and In Vitro Intact Cell Metabolism Assay. Inhibition of COX-2 in intact cells by test compounds was assayed by a previously described method. Human 1483 head and neck squamous cell carcinoma (HNSCC) cells (passage 8-18, mycoplasma negative by a polymerase chain reaction detection method) were cultured in DMEM/F12+10% fetal bovine serum+Antibiotic/Antimycotic in 6-well plates to 60% confluence. Serum-free medium (2 ml) was added, and the cells were treated with inhibitor dissolved in DMSO (0-5 final concentration) for 30 min at 37° C. followed by the addition of [1-$^{14}$C]-arachidonic acid [10 µM, ~55 mCi/mmol] for 20 min at 37° C. Reactions were terminated and analyzed by thin layer chromatography as described above.

Fluorescence microscopy of 1483 HNSCC cells. Fluorescence imaging of human 1483 HNSCC cells by compound 1 was performed by a previously described method. Briefly, human 1483 HNSCC cells were grown to 60% confluence. The cells were incubated in 2.0 ml Hank's balanced salt solution (HBSS)/Tyrode's with 200 nM compound 1 for 30 min at 37° C. The cells were then washed briefly three times and incubated in HBSS/Tyrode's for 30 min at 37° C. Following the required washout period, the cells were imaged in 2.0 ml fresh HBSS/Tyrode's on a Zeiss Axiovert 25 Microscope with the propidium iodide filter (0.5-1.0 sec exposure, gain of 2).

Establishment of xenograft tumors in nude mice. Human 1483 HNSCC cells and HCT116 colorectal carcinoma cells were used to grow tumor xenografts in nude mice using a previously described method. Female nude mice, NU-Foxlnu, were purchased at 6-7 weeks of age from Charles River Labs. Human 1483 HNSCC cells were trypsinized and resuspended in cold PBS containing 30% Matrigel such that 1×10$^6$ cells in 100 µl were injected subcutaneously on the left flank and grew for 2-3 weeks.

In vivo imaging of nude mice with xenografts. Fluorescence imaging of tumors by test compounds was performed by a previously described method. Female nude mice bearing medium-sized 1483 xenograft tumors on the left flank were dosed by intraperitoneal injection with 1 mg/kg compound 1. The animals were lightly anesthetized with 2% isoflurane for fluorescence imaging in the Xenogen IVIS 200 with the DSRed filter at 1.5 cm depth and 1 sec exposure (f2).

In conclusion, the instant inventors have developed a small-molecule nitroxide-based activatable fluorescence probe (compound 1) targeted to COX-2. This probe is non-fluorescent and becomes fluorescent in the intracellular environment of cancer cells in vitro. This non-fluorescent probe is taken up by the COX-2 positive human tumor xenografts, where it reacts with free radicals to become fluorescent, allowing selective visualization of cancerous tissues in vivo.

Example 2—Fluorocoxib Q in Image Guidance of Chemocoxib Delivery in Mouse Model of Orthtopic Breast Cancer Nanomedicine formulations aim to improve the biodistribution and the target site accumulation of systemically applied chemotherapeutics. Various passively and actively targeted nanomedicines have been evaluated over the years, e.g. liposomes, polymers, micelles, and antibodies, and a significant amount of preclinical evidence has been obtained showing that these 5-200 nm sized carrier materials are able to improve the therapeutic index of low-molecular-weight drugs. In addition to therapeutic purposes, nanomedicine formulations have also been used for imaging applications. However, both of these techniques are tested separately and struggling to advance into clinical trials.

Today, the call for personalized medicine demands a new nanoplatform for "co-delivery" of therapeutic and imaging agents in the tumors, allowing imaging to be performed not only before or after, but also during a treatment regimen. Systems and strategies in which disease diagnosis and therapy are combined has been a matter of the top most importance, where COX-2 can play a significant role. In view thereof, the instant inventors tested the hypothesis that a di-block polymer derived micellar nanoparticle can be developed which enables co-loading of "fluorophore probes" and "cytotoxic agents" that are co-targeted to COX-2. These loaded nanoparticle-based systems can be used for co-delivery of pay loads into tumors allowing COX-2-targeted image-guided drug delivery in real-time. This nanoplatform is highly significant not only because it might assist in better understanding various important aspects of the drug delivery process, as well as in developing better drug delivery systems, but also because it might contribute to realizing the potential of personalized medicine, and for the development of more effective and less toxic treatment regimens for individual patients.

As discussed above, selective COX-2 inhibitor fluorocoxib Q (FQ) is a nitroxide analog of fluorocoxib A that exhibits extremely low fluorescence emission due to quenching of the excited electronic state of the carboxy-X-rhodamine (FIG. 28) by the nitroxide radical within the molecule. Upon radical trapping in cancer cells by reacting oxygen species (ROS), these COX-2-targeted probes are fluorescently activated, making them effective for tumors in imaging. To further advance the clinical usefulness of these activatable chemical probes, fluorocoxib Q and chemocoxib A, a COX-2-targeted cytotoxic antitumor agent, were co-loaded into ROS-responsive micellar nanoparticles using clinically applicable di-block copolymers. In the presence of ROS in tumors, these micellar nanoparticles disassemble to co-release both the activatable probe and the cytotoxic agent within the tumor cells. Upon release, the payload binds with intracellular COX-2, where the activatable COX-2 probes become fluorescently activated by ROS allowing visualization of delivery of cytotoxic agent in real-time. This localized fluorescence activation greatly improves sensitivity and specificity of tumor detection with drug delivery.

Synthesis of Fluorocoxib Q Probes—

The carboxylic acid group of fluorocoxib A or B was functionalized by reacting with ethyl chloroformate, followed by treatment with suitably substituted-TEMPO or PROXYL radical bearing compounds to form nitroxide-based activatable conjugates, called fluorocoxib Q probes. Both hydrophobic and hydrophilic tethers of moderate length are used for conjugation (FIG. 28). $^1$H NMR of all intermediate compounds and fluorocoxib Q derivatives are taken on a Bruker AV-I console operating at 400.13 MHz. Mass spectrometric analyses are performed on a Thermo-Electron Surveyor pump TSQ 7000 instrument in ESI positive or negative ion mode.

Synthesis and High Throughput Screening—

Libraries of fluorescent or cytotoxic conjugates of NSAIDs, called fluorocoxibs and chemocoxibs, were designed and synthesized for COX-2-targeted in vivo optical imaging and growth inhibition of tumors, respectively. After synthesis and characterization, each of these compounds was tested for their ability to selectively inhibit COX-2 in assays using both purified proteins and intact cancer cells. High throughput screening identified fluorocoxib A (purified COX-2 $IC_{50}$=0.7 µM, purified COX-1 $IC_{50}$>25 µM, COX-2 positive 1483 HNSCC cells, $IC_{50}$=0.3 µM) and chemocoxib A (purified COX-2 $IC_{50}$=0.29 µM, purified COX-1 $IC_{50}$>25 µM, COX-2 positive 1483 HNSCC cells, $IC_{50}$=0.2 µM) as the most promising COX-2-targted imaging and cytotoxic agents.

X-Ray Crystallography—

The structure of fluorocoxib A and chemocoxib A bound to COX-2 enzyme was successfully crystallized and solved. These complexes crystallized in the $P2_12_12$ space groups and diffracted to 2.6 Å, and 2.2 Å resolution, respectively. The orientation of ligands is clear in both cases, which helped the instant inventors to elucidate the structural basis of these ligands for their selective COX-2 inhibition. In both cases, the indomethacin-part binds at the COX-2 active site while the tether breeches the constriction site. It is noteworthy that the "free carboxyl group" on the phenyl ring of the carboxy-X-rhodamine moiety of fluorocoxib A projects towards an open space located between helices B and D of the COX-2 protein, suggesting feasibility to add additional functionalities on the free carboxyl group without altering the COX-2 binding affinity. On the other hand, the podophyllotoxin-part of chemocoxib A lies underneath helix D that connects the membrane-binding domain of the COX-2 protein (FIG. 29).

Co-Inhibition of COX-2—

COX-2 is a homodimeric enzyme, where one monomer is known as a catalytic subunit and the other as an allosteric subunit. Each subunit contains one active site available for inhibitor binding. Critical examinations of X-ray co-crystal structures show that two molecules of fluorocoxib B (or chemocoxib A) are required for inhibition of a homodimeric COX-2 protien (1 molecule/subunit basis) (FIG. 30A). Thus, it was hypothesized that fluorocoxib Q and chemocoxib A can inhibit COX-2 together while fluorocoxib may bind at the catalytic subunit and chemocoxib at the allosteric subunit or vice versa (FIG. 30B).

In vivo plasma concentrations of FQ: As the amide linkages of FQ are susceptible for cleavage by amidase enzymes, the in vivo stability of these linkages was tested by measuring the plasma concentrations at 0-24 h post-injection of FQ in CD-1 mice. In this experiment, the animals were dosed with FQ (10 mg/kg, i.p.), and blood samples (~0.5 ml)

were collected at 0, 0.5, 1, 3, 6, and 24 h (n=3/time point). Blood samples were centrifuged and plasma samples were collected and stored at −80° C. for quantitative analysis. LC-MS analysis was performed to determine the levels of FQ in the collected plasma at aforementioned time points, where the plasma half-life of FQ was found to be $t_{1/2}$>24 h (FIG. 31), suggesting that the amide linkages of FQ are stable. It is noteworthy that although TEMPO itself exhibits a short half-life, as indicated above, the instant TEMPO conjugate FQ exhibits an in vivo plasma half-life of more than 24 h, indicating that the FQ molecule is stable enough in circulation to allow PK measurements and to reach the target in vivo.

Figure 32A:
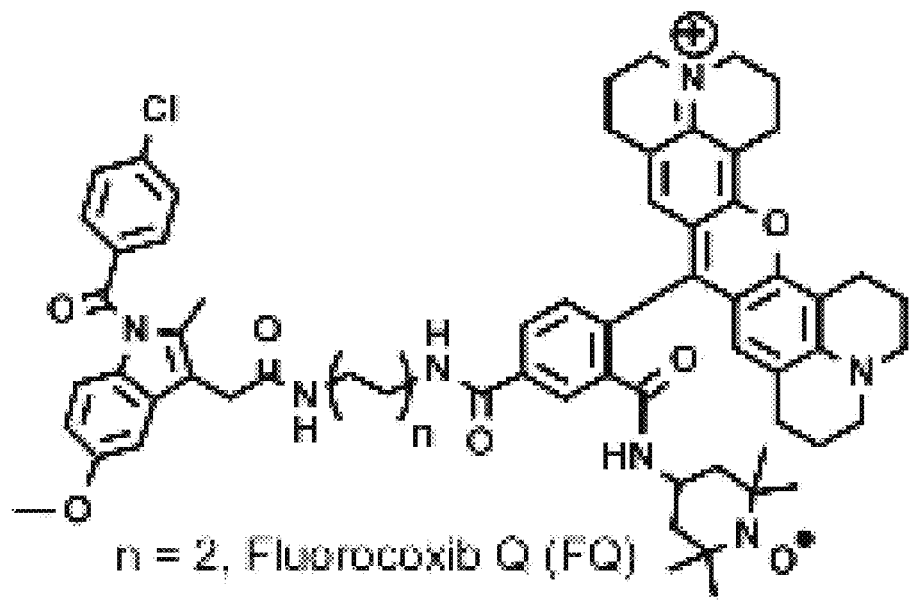
Figure 32B:
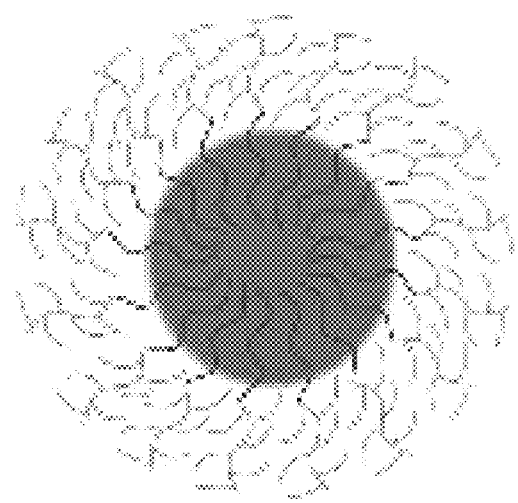

Nanoformulation by Co-Loading of Chemocoxib a (CA) and Fluorocoxib Q (FQ) in Micellar Nanoparticles (CA-FQ-NPs) and their Cell-Based Release, Fluorescence Activation and Cell Death:

$PPS_{135}$-b-$POEGA_{17}$ copolymer was synthesized and chemocoxib A and fluorocoxib Q were co-encapsulated in micellar nanoparticles (CA-FQ-NPs) (FIGS. 32A-B). The CA-FQ-NPs exhibited an average hydrodynamic diameter of 134±4 nm as determined by DLS. To evaluate compound-release, CA-FQ-NPs were incubated with 1483 HNSCC cells expressing COX-2. Signs of FQ release were observed, followed by detectable level of fluorescence activation in 3 h of incubation in these cells, measured by fluorescent microscopy. Also, CA release was observed in these cells when incubated for 48 h, as confirmed by dramatic cell death ($EC_{50}$=64 nM).

In Vivo Image-Guidance of Chemocoxib a Delivery Using Co-Loaded Nanoparticles (CA-FQ-NPs):

To evaluate the ability of CA-FQ-NPs in image-guided delivery of chemocoxib A in breast tumors, 4T1 cells expressing elevated levels of COX-2 enzyme were used. To generate orthotopic breast cancer xenografts, the 4T1 tumor cells ($1\times10^6$ in 200 μL sterile PBS) were injected into the inguinal mammary fat-pads of athymic Balb/C nu/nu female mice (4-6 weeks old, Jax Mice). Tumors were full-grown by 4-5 weeks (tumor volume=length×$width^2$×0.52).

Figure 32C:
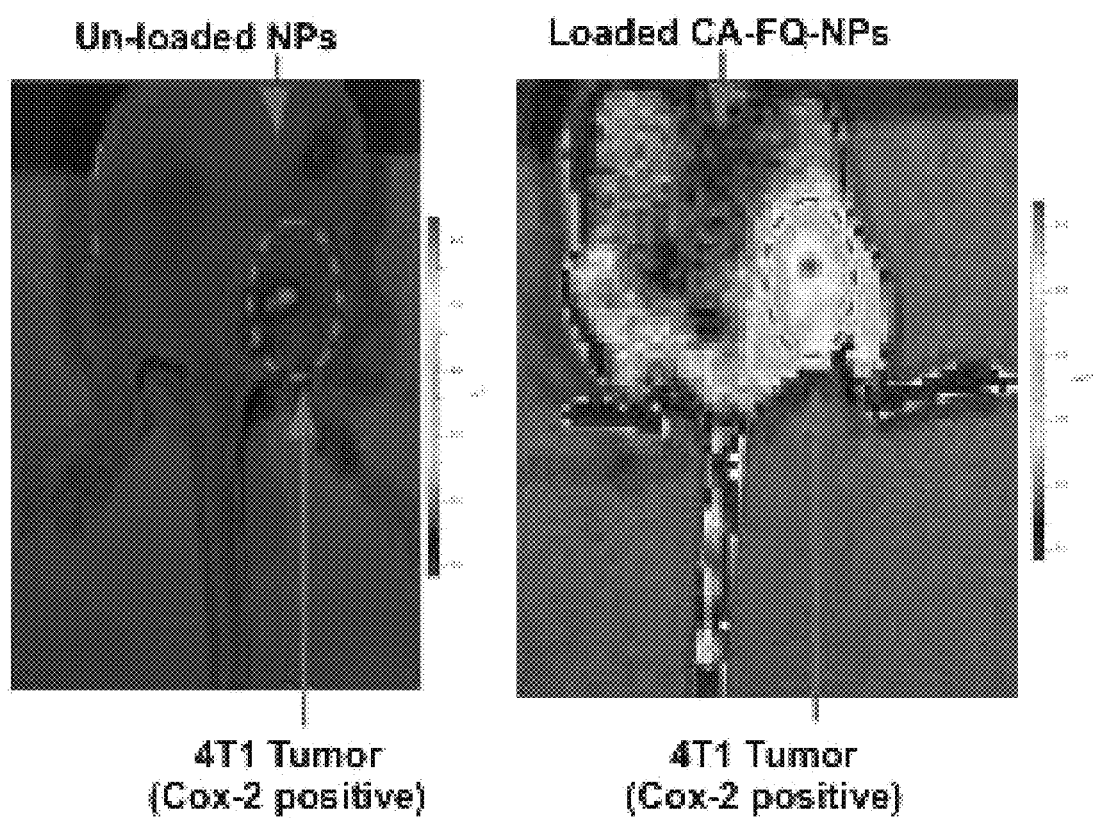
Figure 32D:
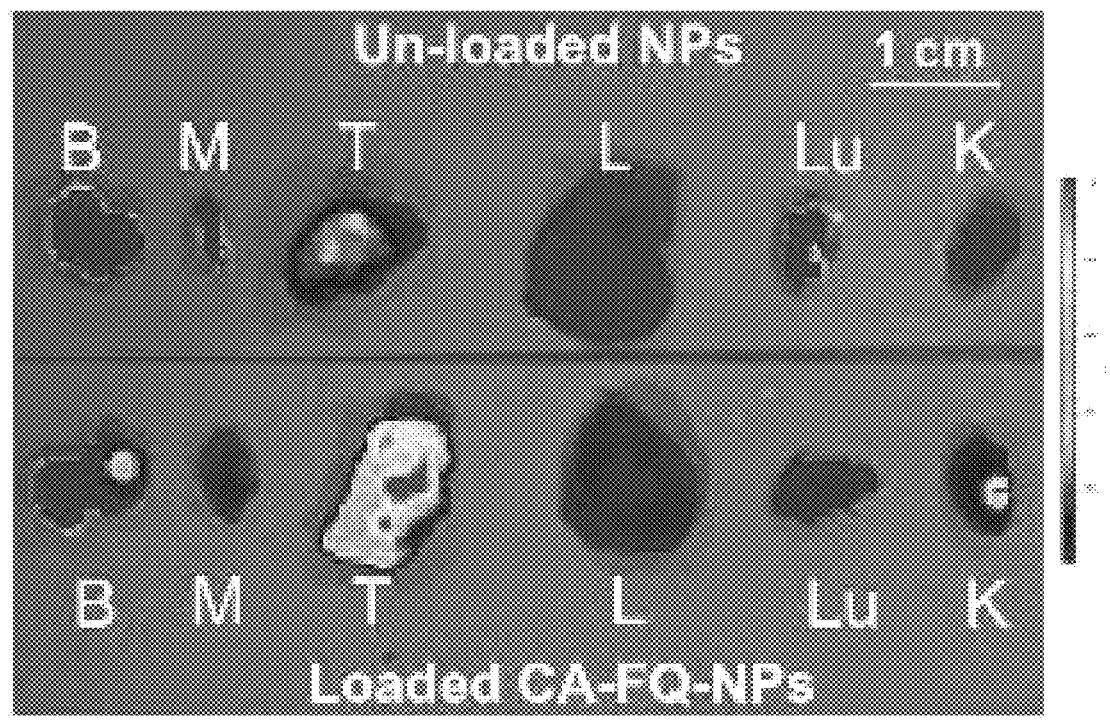
Figure 32E:
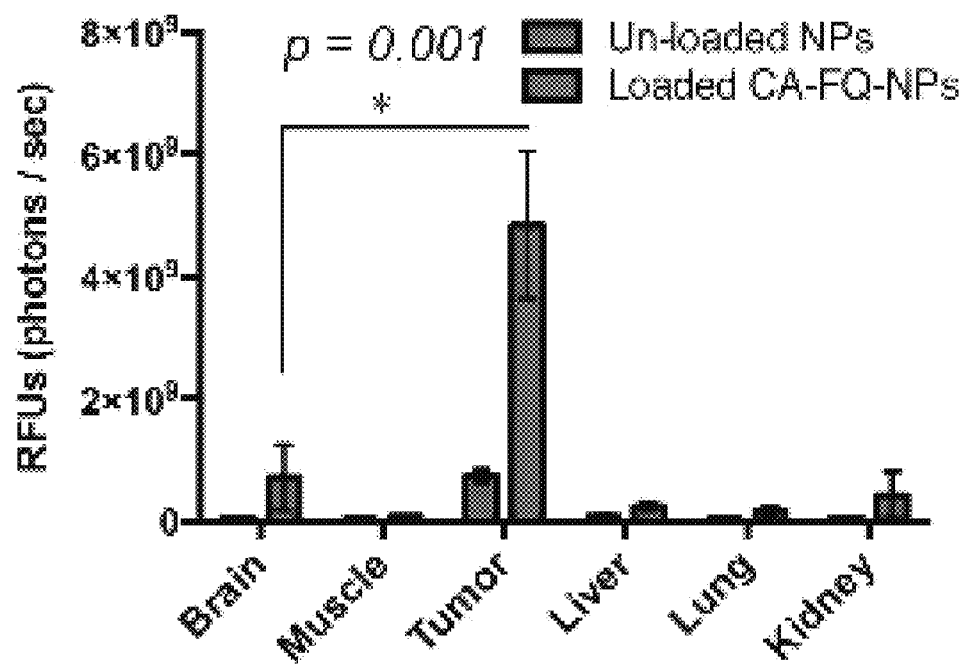

The animals were dosed with CA-FQ-NPs in PBS (1 mg/kg CA, 1 mg/kg FQ, s.c.) and imaged on a Xenogen IVIS200 optical imaging instrument at 0.5 h, 1 h, 3 h, 6 h, 28 h, and 49 h post-injection. While imaging at the 49 h post-injection, a distinctively bright fluorescence was observed in tumors, sign of high tumor uptake and subsequent onsite fluorescence activation of FQ, as compared to tumor fluorescence of animals un-loaded NPs (FIG. 32C). After in vivo imaging, the 49 h animals group was euthanized, and brain, muscle, tumor, liver, lung, and kidney tissues were collected (FIG. 32D). These tissues were imaged ex vivo, where calculated tumor-to-brain ratio was 10:1 as determined from ROI measurements using AMIDE software (p=0.001, n=6) (FIG. 32E). The tumor tissues by LC-MS were homogenized and analyzed, where both CA (3.1 pmol/g tissue) and FQ (0.45 pmol/g tissue) with one of its metabolite (FQ-H, 2.5 pmol/g tissue) were identified in the tumor. These in vivo and ex vivo results suggest that fluorescence FQ-H signals in the tumor are confirmative of the CA delivery in the tumor—a key measure for image-guided drug delivery.

All publications, patents, and patent applications mentioned in this specification are herein incorporated by reference to the same extent as if each individual publication, patent, or patent application was specifically and individually indicated to be incorporated by reference, including the references set forth in the following list:

REFERENCES

1. Hyeran Lee, Walter Akers, Kumar Bhushan, Sharon Bloch, Gail Sudlow, Rui Tang, and Samuel Achilefu. *Near-Infrared pH-Activatable Fluorescent Probes for Imaging Primary and Metastatic Breast Tumors*. Bioconjugate Chem. 2011; 22(4):777-784.
2. Yasuteru Urano, Daisuke Asanuma, Yukihiro Hama, Yoshinori Koyama, Tristan Barrett, Mako Kamiya, Tetsuo Nagano, Toshiaki Watanabe, Akira Hasegawa, Peter L Choyke, and Hisataka Kobayashi. *Selective molecular imaging of viable cancer cells with pH-activatable fluorescence probes*. Nature Med. 2009; 15:104-109.
3. Giri K. Vegesna, Jagadeesh Janjanam, Jianheng Bi, Fen-Tair Luo, Jingtuo Zhang, Connor Olds, Ashutosh Tiwari and Haiying Liu. *pH-Activatable near-infrared fluorescent probes for detection of lysosomal pH inside living cells*. J. Mater. Chem. B. 2014; 2:45004508.
4. Gun-Joong Kim, Doo-Ha Yoon, Mi-Yeon Yun, Hyockman Kwon, Hyun-Joon Haa, Hae-Jo Kim' *An activatable fluorescent probe for targeting cellular membrane through the biothiol-mediated hydrazone-to-pyrazole transformation*. Sensors Actuators B: Chem. 2015; 211: 245-249.
5. Zhang H. Fan J, Wang J, Zhang S, Dou B, Peng X. *An off-on COX-2-specific fluorescent probe: targeting the Golgi apparatus of cancer cells*. J. Am. Chem. Soc. 2013; 135(31):11663-11669.
6. Yamauchi, K.; Yang, M.; Hayashi, K.; Jiang, P.; Yamamoto, N.; Tsuchiya, H.; Tomita, K.; Moossa, A. R.; Bouvet, M.; Hoffman, R. M. *Induction of Cancer Metastasis by Cyclophosphamide Pretreatment of Host Mice: An Opposite Effect of Chemotherapy*. Cancer Res. 2008; 68(2):516-520.
7. Yang, M., Jiang, P. & Hoffman, R. M. *Whole-Body Subcellular Multicolor Imaging of Tumor-Host Interaction and Drug Response in Real Time*. Cancer Res. 2007; 67(11):5195-5200.
8. Wu, A. M. & Senter, P. D. *Arming antibodies: prospects and challenges for immunoconjugates*. Nat. Biotechnol. 2005; 23(9):1137-1146.
9. Samuni, A.; Krishna, C. M.; Riesz, P.; Finkelstein, E.; Russo, A. *A novel metal-free low molecular weight superoxide dismutase mimic*. Biol. Chem. 1988; 263(43): 17921-17924.
10. Kensler, T. W.; Taffe, B. G. *Free radicals in tumor promotion*. Adv. Free Rad. Biol. Med. 1986; 2(2):347-387.
11. Samuni, A. M.; DeGraff, W.; Cook, J. A.; Krishna, M. C.; Russo, A.; Mitchell, J. B. *The effects of antioxidants on radiation-induced apoptosis pathways in TK6 cells*. Free Radical Biol. Med. 2004; 37(10):1648-1655.
12. Mitchell, J. B.; Samuni, A.; Krishna, M. C.; DeGraff, W. G.; Ahn, M. S.; Samuni, U.; Russo, A. *Biologically active metal-independent superoxide dismutase mimics*. Biochemistry. 1990; 29(11):2802-2807.
13. Mitchell, J. B.; DeGraff, W.; Kaufman, D.; Krishna, M. C.; Samuni, A.; Finkelstein, E.; Ahn, M. S.; Hahn, S. M.; Gamson, J.; Russo, A. *Inhibition of oxygen-dependent radiation-induced damage by the nitroxide superoxide dismutase mimic, tempol*. Arch. Biochem. Biophys. 1991; 289(1):62-70.
14. Uddin, M. J., Crews, B. C., Blobaum, A. L., Kingsley, P. J., Gorden, D. L., McIntyre, J. O., Matrisian, L. M., Subbaramaiah, K., Dannenberg, A. J., Piston, D. W., and Marnett, L. J. *Selective Visualization of Cyclooxygenase-2 in Inflammation and Cancer by Targeted Fluorescent Imaging Agents.* Cancer Res. 2010; 70(9):3618-3627.

15. Uddin M. J., Crews B. C., Xu S., Ghebreselasie K., Daniel C. K., Kingsley P. J., Banerjee S., Marnett L. J. *Antitumor Activity of Cytotoxic Cyclooxygenase-2 Inhibitors.* ACS Chem Biol. 2016; 11(11):3052-60.

Neil J. R., Johnson K. M., Nemenoff R. A., Schiemann W. P. *Cox-2 inactivates Smad signaling and enhances EMT stimulated by TGF-beta through a PGE2-dependent mechanisms.* Carcinogenesis. 2008; 29(11):2227-35.

It will be understood that various details of the presently disclosed subject matter can be changed without departing from the scope of the subject matter disclosed herein. Furthermore, the foregoing description is for the purpose of illustration only, and not for the purpose of limitation.

What is claimed is:

1. A compound comprising a structure according to formula I:

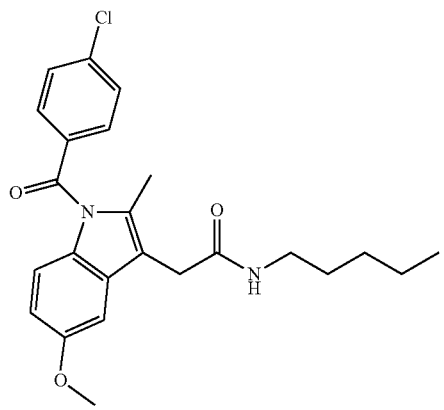

(I)

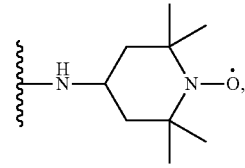

wherein R is selected from O⁻,

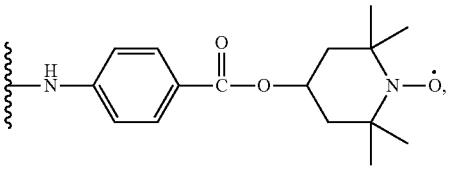

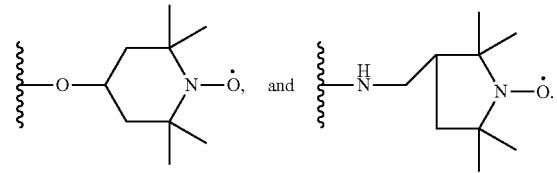

2. The compound of claim 1, wherein the compound comprises the following structure:

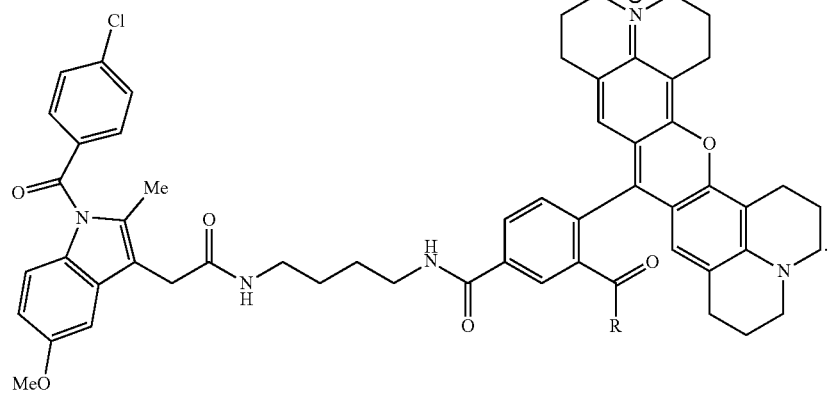

3. The compound of claim 1, wherein the compound comprises the following structure:
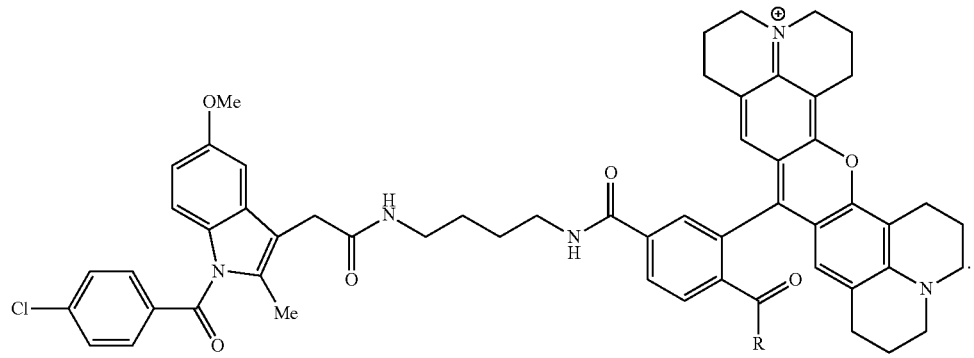
4. The compound of claim 1, wherein R is selected from the group consisting of
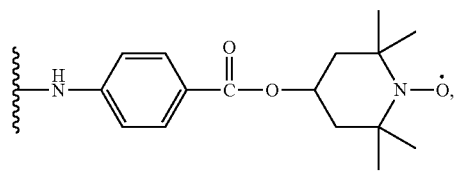
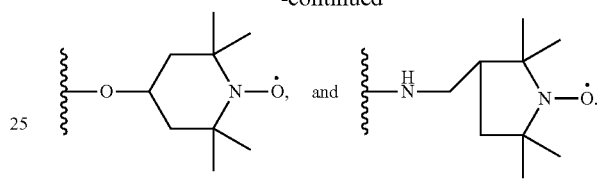
-continued
5. The compound of claim 4, wherein R is
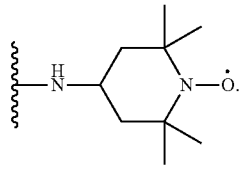
6. The compound of claim 5, wherein the compound has the following structure:
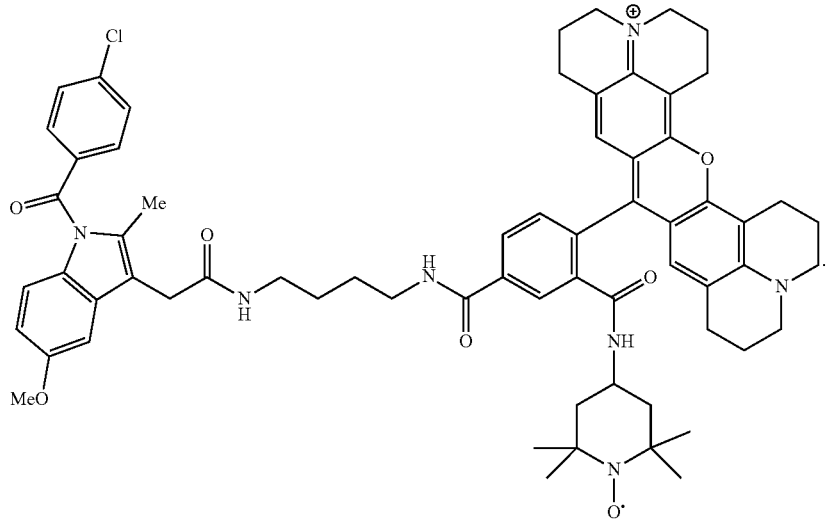

7. The compound of claim 5, wherein the compound has the following structure:

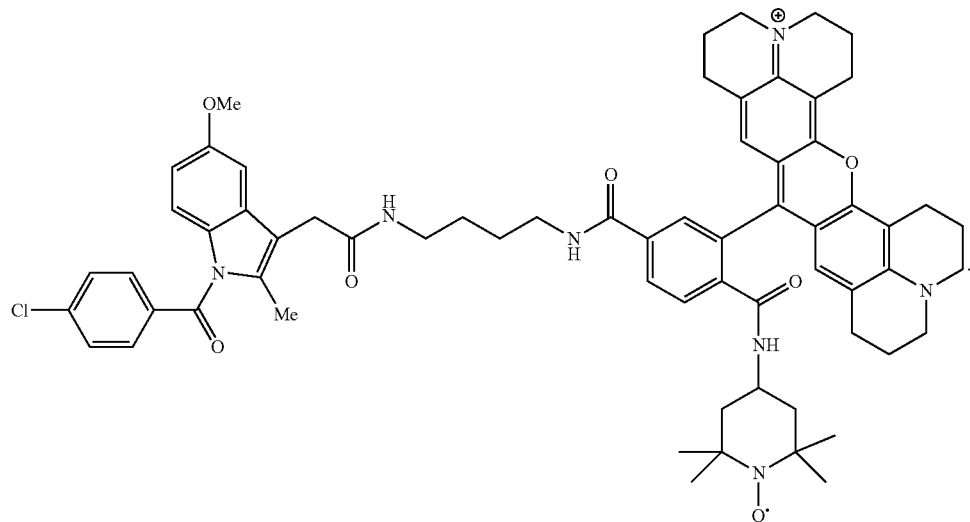

8. The compound of claim 4, wherein R is

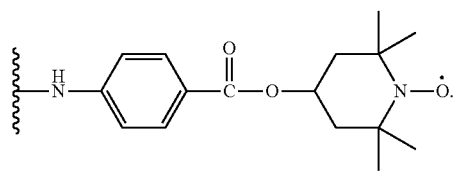

9. The compound of claim 8, wherein the compound is a 5-isomer.

10. The compound of claim 8, wherein the compound is a 6-isomer.

11. The compound of claim 4, wherein R is

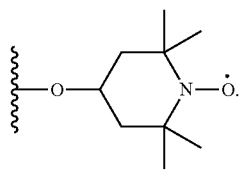

12. The compound of claim 11, wherein the compound is a 5-isomer.

13. The compound of claim 11, wherein the compound is a 6-isomer.

14. The compound of claim 4, wherein R is

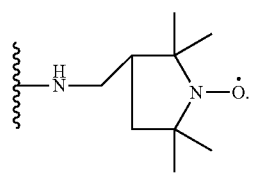

15. The compound of claim 14, wherein the compound is a 5-isomer.

16. The compound of claim 14, wherein the compound is a 6-isomer.

17. A method of imaging a cell, the method comprising administering the compound of claim 1 and then imaging one or more cells contacted with the compound.

18. The method of claim 17, wherein the cell is a tumor cell.

19. The method of claim 18, wherein the tumor cell is in vivo.

20. A method of detecting a cancer, an inflammatory disease, or a neoplastic disease, the method comprising administering the compound of claim 1 and then imaging one or more cells contacted with the compound.

* * * * *

UNITED STATES PATENT AND TRADEMARK OFFICE
CERTIFICATE OF CORRECTION

| | | |
|---|---|---|
| PATENT NO. | : 10,792,377 B2 | Page 1 of 1 |
| APPLICATION NO. | : 15/944735 | |
| DATED | : October 6, 2020 | |
| INVENTOR(S) | : Uddin et al. | |

It is certified that error appears in the above-identified patent and that said Letters Patent is hereby corrected as shown below:

In the Specification

Replace the second paragraph, which appears on Column 1, with the following:
Government Interest
This invention was made with government support under Grant Numbers CA089450 and CA136465, awarded by the National Institutes of Health. The Government has certain rights in the invention.

Signed and Sealed this
Twenty-sixth Day of August, 2025

Coke Morgan Stewart
*Acting Director of the United States Patent and Trademark Office*